US012588687B2

(12) United States Patent
Suarez Garcia et al.

(10) Patent No.: US 12,588,687 B2
(45) Date of Patent: Mar. 31, 2026

(54) MICROBIAL CELL PRODUCT, METHOD FOR OBTAINING SAID MICROBIAL CELL PRODUCT AND USE OF SAID MICROBIAL CELL PRODUCT

(71) Applicant: FUMI INGREDIENTS B.V., Wageningen (NL)

(72) Inventors: Edgar Suarez Garcia, Wageningen (NL); Corjan Vandenberg, Wageningen (NL)

(73) Assignee: FUMI INGREDIENTS B.V., Wageningen (NL)

( * ) Notice: Subject to any disclaimer, the term of this patent is extended or adjusted under 35 U.S.C. 154(b) by 338 days.

(21) Appl. No.: 18/245,767

(22) PCT Filed: Sep. 13, 2021

(86) PCT No.: PCT/EP2021/075137
§ 371 (c)(1),
(2) Date: Mar. 17, 2023

(87) PCT Pub. No.: WO2022/058287
PCT Pub. Date: Mar. 24, 2022

(65) Prior Publication Data
US 2023/0389568 A1      Dec. 7, 2023

(30) Foreign Application Priority Data
Sep. 18, 2020    (NL) ...................................... 2026504

(51) Int. Cl.
*A23J 1/18*        (2006.01)
*A23J 3/20*        (2006.01)
(Continued)

(52) U.S. Cl.
CPC . *A23J 1/18* (2013.01); *A23J 3/20* (2013.01); *A23J 3/225* (2013.01); *C12N 1/063* (2013.01);
(Continued)

(58) Field of Classification Search
CPC . C12N 1/066; C12N 1/063; C12N 1/06; A23J 3/20; A23J 1/18
(Continued)

(56) References Cited

U.S. PATENT DOCUMENTS

| | | | |
|---|---|---|---|
| 3,888,839 A | 6/1975 | Newell et al. | |
| 5,756,135 A * | 5/1998 | Seeley ................... | A23L 33/14 |
| | | | 435/254.2 |

(Continued)

FOREIGN PATENT DOCUMENTS

| | | |
|---|---|---|
| EP | 1199353 A1 | 4/2002 |
| EP | 2774993 A1 | 9/2014 |

(Continued)

OTHER PUBLICATIONS

International Search Report and Written Opinion for Application No. PCT/EP2021/075137 dated Nov. 25, 2021 (17 pages).

(Continued)

*Primary Examiner* — Jennifer McNeil
(74) *Attorney, Agent, or Firm* — Michael Best & Friedrich LLP

(57)        ABSTRACT

The present invention relates to a method for preparing a microbial cell product, said method comprising: providing an aqueous suspension comprising microbial cells; subjecting said suspension to mechanical cell disintegration at a temperature in the range of 15-35° C., preferably at a pH value in the range of 9-11, to obtain an aqueous suspension comprising disintegrated microbial cells; separating the suspension to provide an extract enriched in small cell fragments, and an extract enriched in large cell fragments; and combining at least a portion of each extract, to provide said microbial cell product. The invention further relates to a microbial cell product obtained or obtainable with said method. The invention further relates to the use of said
(Continued)

product in foodstuffs, for example as a substitute for egg-white; in animal foodstuffs; and/or in cosmetic formulations.

20 Claims, 13 Drawing Sheets

(51) Int. Cl.

| | |
|---|---|
| *A23J 3/22* | (2006.01) |
| *C12N 1/06* | (2006.01) |
| *C12N 1/063* | (2026.01) |
| *C12N 1/066* | (2026.01) |
| *C12R 1/865* | (2006.01) |

(52) U.S. Cl.
CPC ........ *C12N 1/066* (2013.01); *C12R 2001/865* (2021.05)

(58) Field of Classification Search
USPC ......................................................... 426/656
See application file for complete search history.

(56) References Cited

U.S. PATENT DOCUMENTS

2019/0352676 A1* 11/2019 Senaratne ................. C12P 7/54

2020/0095292 A1    3/2020  Patinier
2020/0397021 A1* 12/2020  Henderson, Jr. ........ A23J 1/008

FOREIGN PATENT DOCUMENTS

| | | | |
|---|---|---|---|
| EP | 3670646 | A1 | 6/2020 |
| GB | 1460030 | A | 12/1967 |
| WO | 2010045368 | A2 | 4/2010 |
| WO | 2013067453 | A1 | 5/2013 |
| WO | 2016077457 | A1 | 5/2016 |
| WO | 2017102535 | A1 | 6/2017 |
| WO | 2018115042 | A1 | 6/2018 |
| WO | 2019226707 | A1 | 11/2019 |

OTHER PUBLICATIONS

Fujitani F et al: "Yeast protein with gelling property, used as food material—prepd. by extracting crushed, washed yeast with alkaline soln. then precipitating the extracted material", WPI / 2017 Clarivate Analytics,, vol. 1979, No. 5, Dec. 19, 1978 (Dec. 19, 1978) (1 page).
Lowry, O. H.; et al. (1951). "Protein measurement with the Folin phenol reagent". Journal of Biological Chemistry. 193 (1): 265-75.
Dubois, M. et al. "Colorimetric method for determination of sugars and related substances." Analytical chemistry 28.3 (1956): 350-356.

* cited by examiner

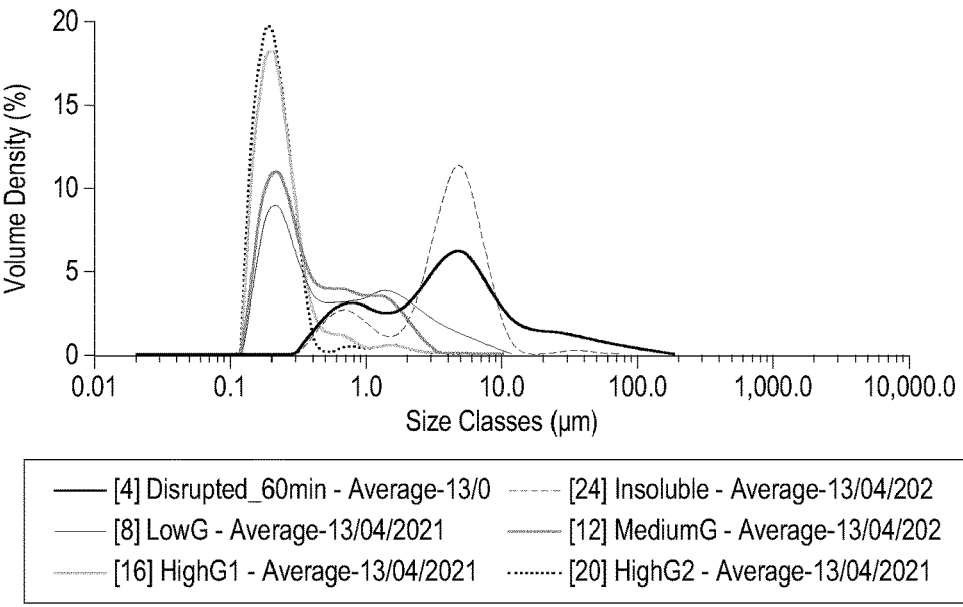
FIG. 12
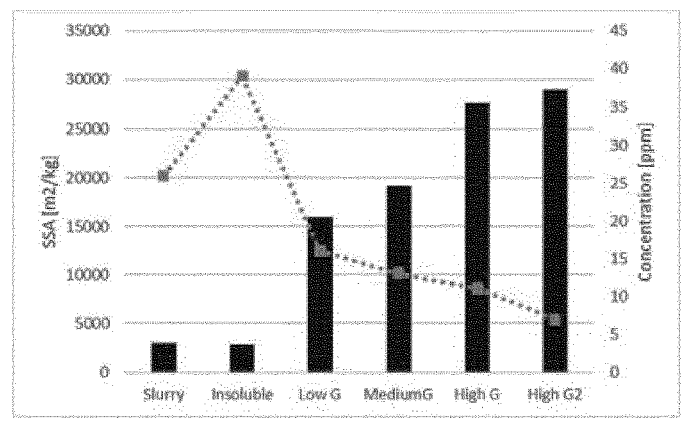
Fig 13
FIG. 13
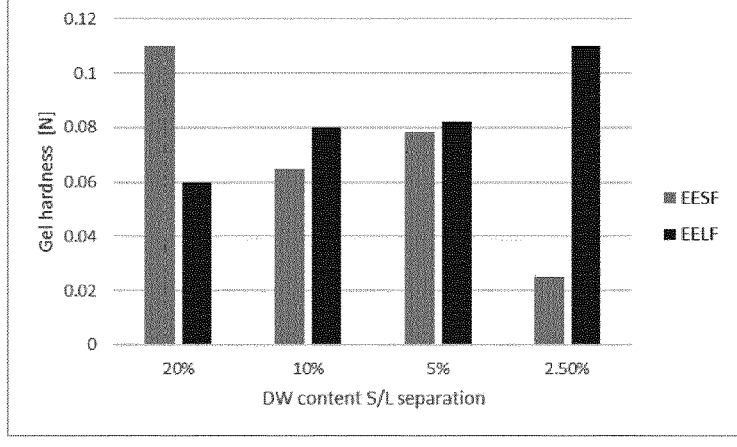
FIG. 14

——[3]    SN_Oxdill - Average-15/04/2021        ——[15]    10% SN - Average-16/04/2021

——[19]   5%_SN - Average-16/04/2021        ——[23]    2.5%_SN - Average-16/04/2021

——[27]   1.25%_SN - Average-16/04/2021

MICROBIAL CELL PRODUCT, METHOD FOR OBTAINING SAID MICROBIAL CELL PRODUCT AND USE OF SAID MICROBIAL CELL PRODUCT

RELATED APPLICATION DATA

This application is a U.S. national phase application of International Application No. PCT/EP2021/075137 filed Sep. 13, 2021, which claims priority to Application No. NL 2026504 filed Sep. 18, 2020, the entire contents of which are herein incorporated by reference herein.

TECHNICAL FIELD

The present invention relates to method for obtaining a microbial cell product. The invention further relates to a microbial cell product obtained by or obtainable by said method. The invention further relates to the use of said microbial cell product.

BACKGROUND

Eggs are a versatile and near ubiquitous food and food component. Eggs are highly valued for numerous reasons. Eggs not only provide high nutritional content, they are also an essential component of a wide range of food products, ranging from, but not limited to: breads, cakes, cookies, custards, soufflés, muffins, scones, biscuits, pasta, dressings, sauces, and ice cream.

Egg white makes up around two-thirds of a chicken egg by weight. Egg white consists primarily of about 90% water into which about 10% proteins (including albumins, muco-proteins, and globulins) are dissolved. Unlike the yolk, which is rich in lipids (fats), egg white contains almost no fat, and carbohydrate content is less than 1%. Egg whites contain about 56% of the protein in the egg. Egg white has many uses in food (e.g. meringue, mousse) and also many other uses (e.g. in the preparation of vaccines such as those for influenza).

The use of eggs has a number of drawbacks. For example, eggs contain high levels of cholesterol and saturated fats, which increases risk for cardiovascular diseases and obesity. Other consumers that would benefit from the high nutritional content and enjoyment of egg-containing products may be prevented from doing so due to food allergies or other dietary restrictions. For instance, 1-2% of young children are estimated to be allergic to eggs. Significant population segments follow voluntary dietary restrictions, e.g., vegans, and others may not eat eggs for reasons of avoiding animal exploitation or for religious or other reasons. In addition, the industrial scale production of eggs is associated with indus-trial farming of chickens, which incur high costs, such as, e.g., costs related to food health and safety restrictions for farmers, high transportation costs, and the cost of feeding and housing egg-laying birds. Furthermore, industrial chicken farming has a negative environmental impact, and raises a number of important humanitarian issues.

Furthermore, eggs have limited shelf life, and are at risk of harboring infectious pathogens, such as, for example, *Salmonella, E. coli*, and other pathogens which may endanger public health.

Many attempts have been made to create an egg substitute (either full egg substitute or egg-white substitute) that reca-pitulates the desired features of natural eggs while minimiz-ing the unwanted features of eggs. Egg substitutes aim to achieve similar binding properties, moisturizing properties, emulsifying properties and/or leavening properties as eggs, or as egg-whites.

There are many home-cooking based substitutes, e.g., mashed bananas, applesauce, aquafaba (cooking liquid of chickpeas) or flax seeds to replace eggs in baking; baking powder/baking soda mixtures to provide leavening; and flour/water mixtures to provide binding and leavening.

Further, industrially produced plant-based egg substitutes are for instance known from WO2013067453A1, disclosing beans or peas as the starting material. WO2017102535A1 discloses a process to obtain a gluten free native rapeseed protein isolate comprising <10 ppm gliadin, which may be used in any human nutritional food applications including as a foaming agent to replace egg whites. An alternative egg-free, egg white protein production method is disclosed in WO2016077457A1, the method comprising recombinant expression of two or more egg white proteins; and mixing the two or more egg white proteins. WO2010045368A2 discloses food compositions comprising microalgal bio-mass, whole microalgal cells, and/or microalgal oil in com-bination with one or more other edible ingredients.

The above-mentioned full egg and egg-white substitutes only partly have the desired combination of properties of egg-white that allow a versatile use of the composition in (food) products.

Therefore, there is a need for an improved substitute for egg-white. There is a further need for an egg-free compo-sition that can be used as binding agent, moisturizing agent, emulsifying and/or oil/water holding agent.

SUMMARY

It is an object of the present invention to provide an egg-free composition that can be used as binding agent, gelation agent, thickening agent, foaming agent, moisturiz-ing agent, emulsifying and/or oil/water holding agent. It is a further object of embodiments of the present invention to provide an improved composition for use in foodstuffs, for example as a substitute for egg-white; in animal foodstuffs, for example pelleted, dry/powders, semi-moist or wet feed formulations; and/or in cosmetic formulations, for example solutions, creams, lotions, suspensions, ointments/pastes, powders and gels.

The invention relates in a first aspect to a method for preparing a microbial cell product. The inventive method comprises i) providing an aqueous suspension comprising microbial cells; ii) subjecting said suspension to mechanical cell disintegration, to obtain an aqueous suspension com-prising disintegrated microbial cells; iii) separating the sus-pension to provide an extract enriched in small cell frag-ments, and an extract enriched in large cell fragments; and v) combining at least a portion of each extract, to provide a microbial cell product.

The present inventors have found that by separating the suspension into two distinct extracts, and recombining each extract, a microbial cell product having different properties to a simple suspension can be produced. Further, it is believed that by altering either or both of the disintegration step and the proportions of recombined extract, then the final properties of the microbial cell product can be altered. This allows fine tuning of the product so as to make it more or less suitable for a particular use. An additional "fine tuning" step can include incubating the composition for a time between certain steps of the method; for example, prior to recom-bining the extracts.

Further details of this fine tuning, and of the other steps of the method, are described in more detail herein.

The invention also relates to a microbial cell product capable of being produced in this way, as well as to a food product comprising such a microbial cell product. Other features and aspects of the invention will be apparent from the detailed description.

The invention relates in another aspect to a method for preparing a microbial cell product. The inventive method comprises i) providing an aqueous suspension comprising microbial cells; and ii) subjecting said suspension to mechanical cell disintegration, to obtain an aqueous suspension comprising disintegrated microbial cells as said microbial cell product. The mechanical cell disintegration according to the present method takes place at a temperature in the range of 1-45° C.

In a further aspect, the invention relates to a microbial cell product directly obtained by or obtainable by the method according to the present invention.

In a further aspect, the invention relates to an extract enriched in small cell fragments and an extract enriched in large cell fragments obtainable by the method according to the present invention.

In a further aspect, the invention relates to the use of the microbial cell product according to the invention as emulsifier, foaming agent, binding agent, leavening agent, thickening agent, moisturizing agent, adhesive, browning agent, clarification agent, gelation agent, crystallization control agent, humectant agent, tenderizer, aeration agent, structure improvement agent, coagulation agent, coating agent, colorant, gloss agent, flavoring, freezing agent, insulation agent, mouthfeel improvement agent, pH buffer, shelf life extension agent, fat replacer, meat extender, preservative, antimicrobial, food spoilage inhibitor, malolactic fermentation inhibitor, texture improvement agent, egg replacement, or any combination thereof.

In a further aspect, the invention relates to the use of the microbial cell product according to the invention in an edible egg-free emulsion, egg analog, egg-free scrambled eggs, egg-free patty, egg-free pound cake, egg-free angel food cake, egg-white free meat-replacer, egg-free meat-replacer, egg-free yellow cake, egg- and dairy-free cream cheese, egg-free pasta dough, egg-free custard, egg-free ice cream, or in a dairy-free milk.

Corresponding embodiments disclosed for the method are also applicable for the microbial cell product according to the present invention, the extract enriched in small cell fragments, the extract enriched in large cell fragments, according to the invention, and the use of the microbial cell product according to the present invention.

LIST OF DEFINITIONS

The following definitions are used in the present description and claims to define the stated subject matter. Other terms not cited below are meant to have the generally accepted meaning in the field.

"Drying" as used in the present description means reducing the moisture content. The term drying includes partial drying wherein moisture may remain after drying in a reduced amount, which can also be seen as concentrating.

"Dry weight (DW)" and "dry cell weight" as used in the present description mean weight determined in the relative absence of water. For example, reference to microbial biomass as comprising a specified percentage of a particular component by dry weight means that the percentage is calculated based on the weight of the biomass after substantially all water has been removed.

"Disruption" as used in the present description in the context of microbial cells is also referred to as "lysing" and means opening the cells to release cytoplasmic compounds (also referred to as the "lysate").

"Disintegration" as used in the present description means, in the context of disintegration of microbial cells, the fragmentation of the cells. This implies that the average size of the resulting cell fragments must be smaller than the average cell size of the initial microbial cells. Disintegration can be seen as a specific type of disrupting in which not only the cells are opened, but in which the cells are also fragmented.

"Cytoplasmic material" or "Cytoplasmic compounds" as used in the present invention means all material that is usually contained within a cell, enclosed by the cell membrane, except for the cell nucleus (if present). When a cell is disintegrated or disrupted, the cytoplasmic material is released from the cell.

"Microbial cells" as used in the present description means: microbes. This can be eukaryotic and prokaryotic unicellular organisms and colonies of them. A prokaryote is a cellular organism that lacks an envelope-enclosed nucleus. In the three-domain system, based upon molecular analysis, prokaryotes are divided into two domains: Bacteria (formerly Eubacteria) and Archaea (formerly Archaebacteria). Organisms with nuclei are placed in a third domain, Eukaryota. Microbial cells according to the present invention also encompass algae and fungi such as yeast.

"Microorganism" and "microbe" as used in the present description mean any microscopic colonial or unicellular organism.

"Microbial cell product" as used in the present description means: a product derived from microbial cells that is obtained by processing microbial cells in a certain manner.

"Extract enriched in small cell fragments (EESF)" as used in the present invention means a microbial cell product that is obtained by separation of the aqueous suspension comprising disintegrated microbial cells. During this separation an extract is separated out of the aqueous suspension comprising disintegrated microbial cells leaving behind an aqueous suspension comprising disintegrated microbial cells that is partly depleted from small cell fragments. In other words, the separation treatment produces an extract enriched in small cell fragments (as main product) and an aqueous suspension depleted in small cell fragments, the latter can and will also be referred to as an extract enriched in large cell fragments. "Small cell fragments" as used in the present description means cell fragments obtained from disintegration of microbial cells having a size of equal to or less than $d50 \leq 500$ nanometers (nm).

"Extract enriched in large cell fragments (EELF)" or "aqueous suspension depleted in small cell fragments" as used in the present invention means a microbial cell product that is obtained by separation of the aqueous suspension comprising disintegrated microbial cells. During this separation an extract is separated out of the aqueous suspension comprising disintegrated microbial cells leaving behind an aqueous suspension comprising disintegrated microbial cells that is partly depleted from small cell fragments. In other words, the separation treatment produces an extract enriched in small cell fragments (as main product) and an aqueous suspension depleted in small cell fragments (as by product), the latter can and will also be referred to as an extract enriched in large cell fragments. "Large cell fragments" as used in the present description means cell fragments obtained from disintegration of microbial cells having a size more than d50≥500 nanometer (nm).

"Microbial biomass" and "biomass" as used in the present description mean a material produced by growth and/or propagation of microbial cells, or produced as byproduct of fermentation processes. Biomass may contain cells and/or intracellular contents as well as extracellular material. Extracellular material includes, but is not limited to, compounds secreted by a cell.

"Bead milling" as used in the present description means agitation of microbial cells in suspension with small abrasive particles (beads). Cells break because of shear forces, grinding between beads, and collisions with/between beads. Shear forces produced by the beads disrupt the cells and cause disintegration with concomitant release of cellular compounds.

"Centrifugation" as used in the present description means the application of centrifugal force to separate particles from a solution according to their size, shape, density, viscosity of the medium and rotor speed, among other parameters. The rate of centrifugation is specified by the angular velocity usually expressed as revolutions per minute (RPM), or acceleration expressed as g. The conversion factor between RPM and g depends on the radius of the centrifuge rotor. The general formula for calculating the revolutions per minute (RPM) of a centrifuge is $$RPM = \sqrt{\frac{g}{r}}$$

where g represents the respective force of the centrifuge and r the radius from the center of the rotor to a point in the sample. However, depending on the centrifuge model used, the respective angle of the rotor and the radius may vary, thus the formula gets modified. The most common formula used for calculating Relative Centrifugal Force is:

$$RCF(*g) = 1.118 * r * \left(\frac{RPM}{1000}\right)^2$$

wherein r is the radius in mm.

BRIEF DESCRIPTION OF DRAWINGS

The present invention is described hereinafter with reference to the accompanying drawings in which embodiments of the present invention are shown and in which like reference numbers indicate the same or similar elements.

FIG. 12 shows particle size distribution for different fractions of a yeast preparation under different separation intensities.

FIG. 13 shows specific surface area and concentration of different fractions of a yeast preparation under different separation intensities.

FIG. 14 shows gel hardness of the EESF and EELF of a yeast preparation under separation at different dilution conditions.

DESCRIPTION OF EMBODIMENTS

As stated above, the invention relates in a first aspect to a method for preparing a microbial cell product, said method comprising i) providing an aqueous suspension comprising microbial cells; ii) subjecting said suspension to mechanical cell disintegration, to obtain an aqueous suspension comprising disintegrated microbial cells; iii) separating the suspension to provide an extract enriched in small cell fragments, and an extract enriched in large cell fragments; and v) combining at least a portion of each extract, to provide a microbial cell product. The mechanical cell disintegration can be carried out at a temperature in the range of 1-45° C. (viz. in the range of 1° C. up to and including 45° C.), preferably 15-35° C., and more preferably around 25° C. to obtain an aqueous suspension comprising disintegrated microbial cells.

Figure 1:
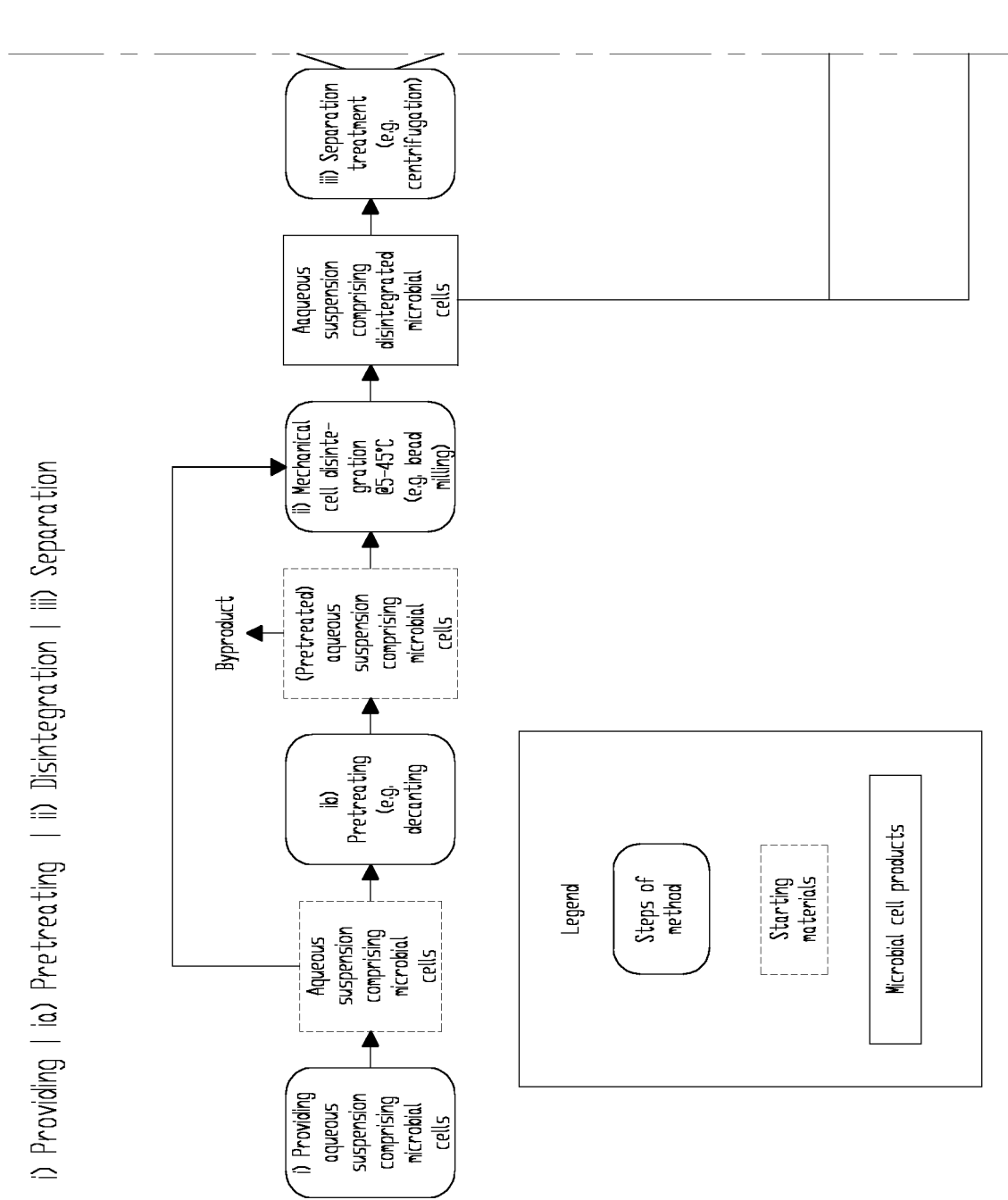
FIG. 1 shows an overview of the different (optional) steps of the method according to the invention, and the obtained (intermediate) products. This overview shows many different routes to obtain microbial cell products according to the present invention.
Figure 1:
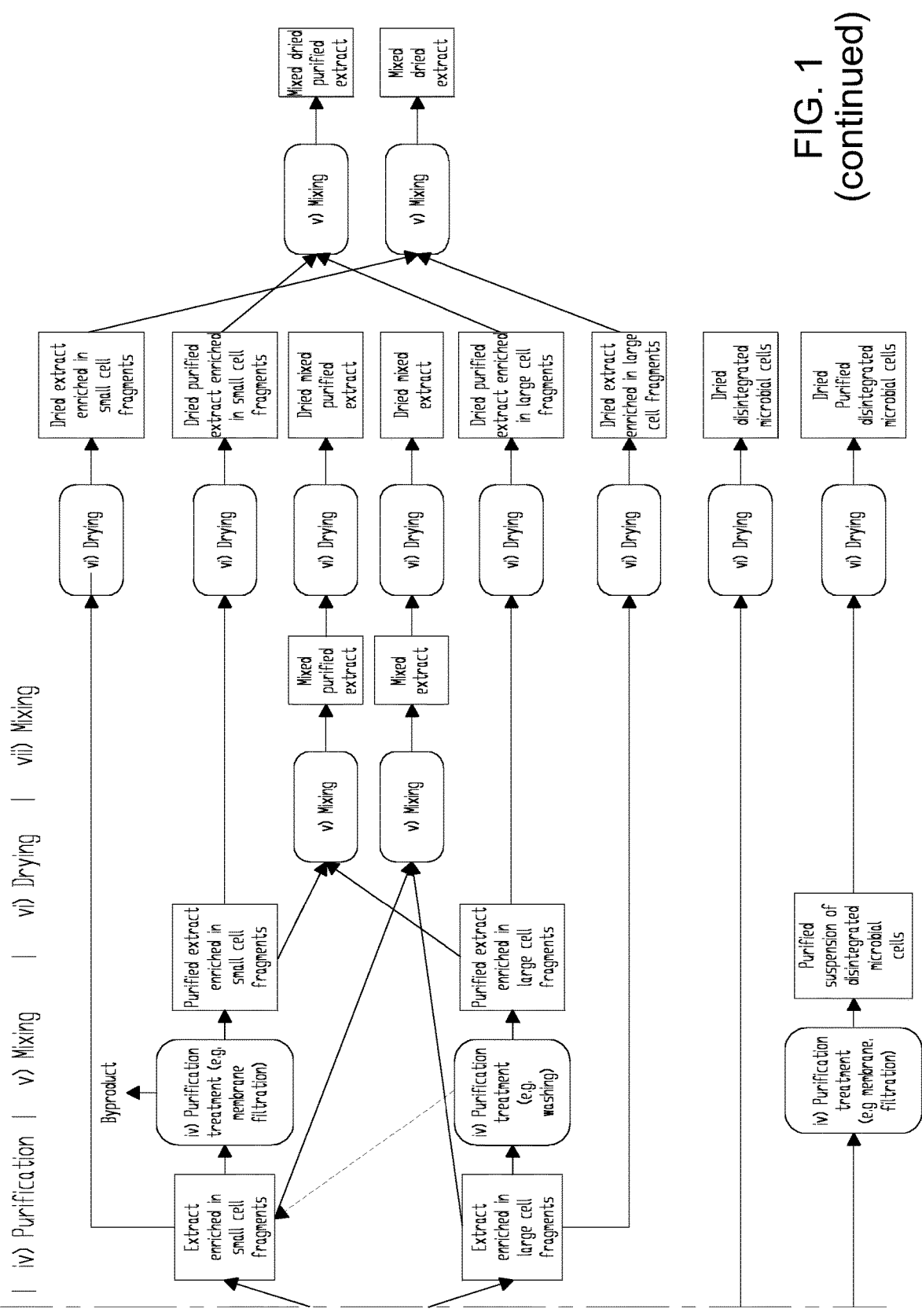
Figure 8:
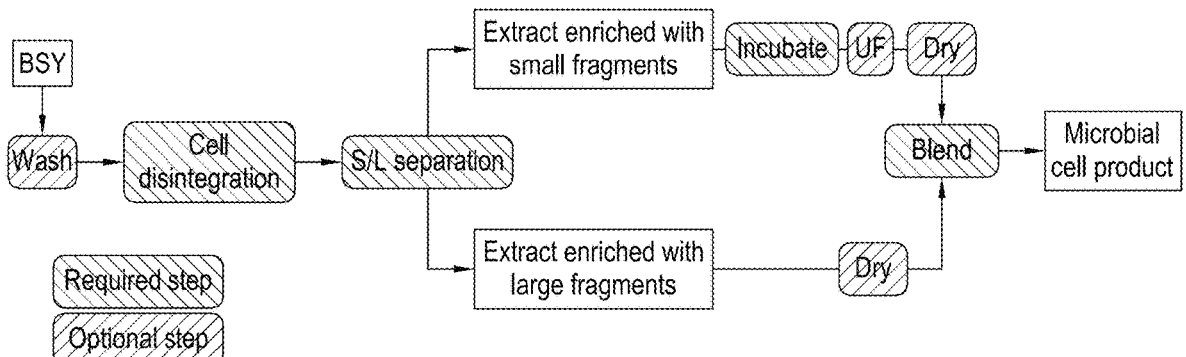
FIG. 8 shows a simplified process flow diagram for preparing a microbial cell product according to an embodiment of the invention.

In FIG. 1 the step of providing said aqueous suspension (step i) is shown in grey on the left-hand side. Step ii) is disclosed in grey somewhat left from the middle. After step i) the aqueous suspension can be either directly subjected to step ii) or first a pretreatment (step ia)) is carried out. For each of the different routes (disclosed in FIG. 1 and disclosed below) this optional step of pretreatment may be present. The product from step ii) is an aqueous suspension comprising disintegrated microbial cells. The aqueous suspension is then separated (iii) so as to provide into an extract enriched in small fragments (EESF) and an extract enriched in large cell fragments (EELF), in addition to soluble compounds in which the fractions are suspended. Portions of the enriched extracts are then combined (v) to provide a microbial cell product. This may in some instances herein be referred to as a mixed extract. The process is additionally illustrated in FIG. 8.

The method optionally comprises any of the steps ia) pretreatment, iv) purification treatment, vi) drying and vii) mixing. For example, the method may comprise steps i) and ii); or steps i), ia) and ii); or steps i), ia), ii) and iii); or steps i), ia), ii), iii) and iv); or steps i), ia), ii), iii), iv) and v); or steps i), ia), ii), iii), iv), v) and iv); or steps i), ia), ii), iii), iv), v), vi) and vii).

Microbial cell products obtainable with the method according to the present invention include: a mixed extract, a mixed purified extract, a dried mixed extract, a dried mixed purified extract, a mixed dried extract, and a mixed dried purified extract With microbial cell products also purified microbial cell products and dried microbial cell products are meant.

The purified microbial cell products obtainable with the method according to the present invention include a mixed purified extract, a dried mixed purified extract, and a mixed dried purified extract.

Dried microbial cell products obtainable with the method according to the present invention include a dried mixed extract, a dried mixed purified extract, a mixed dried extract, and a mixed dried purified extract.

Certain steps of the method described herein may be carried out to obtain alternative products, distinct from the mixed extract obtained from the method of the invention. For example, and referring to the steps in FIG. 1, a purified suspension of disintegrated microbial cells is obtained after carrying out the following subsequent steps: step i), step ii), and step iv); or step i), step ia), step ii), and step iv).

Dried purified disintegrated microbial cells are/is obtained after carrying out the following subsequent steps: step i), step ii), step iv) and step vi); or step i), step ia), step ii), step iv) and step vi).

Dried disintegrated microbial cells are/is obtained after carrying out the following subsequent steps: step i), step ii), and step vi) or step i), step ia), step ii), and step vi).

An extract enriched in small cell fragments is obtained after carrying out the following subsequent steps: step i), step ii) and step iii); or step i), step ia), step ii) and step iii).

An extract enriched in large cell fragments is obtained after carrying out the following subsequent steps: step i), step ii) and step iii); or step i), step ia), step ii) and step iii).

A dried extract enriched in small cell fragments is obtained after carrying out the following subsequent steps: step i), step ii), step iii) and step vi) on the extract enriched in small cell fragments or step i), step ia), step ii), step iii) and step vi) on the extract enriched in small cell fragments.

A dried extract enriched in large cell fragments is obtained after carrying out the following subsequent steps: step i), step ii), step iii) and step vi) on the extract enriched in large cell fragments; or step i), step ia), step ii), step iii) and step vi) on the extract enriched in large cell fragments.

A purified extract enriched in small cell fragments is obtained after carrying out the following subsequent steps: step i), step ii), step iii) and step iv) on the extract enriched in small cell fragments; or step i), step ia), step ii), step iii) and step iv) on the extract enriched in small cell fragments.

A purified extract enriched in large cell fragments is obtained after carrying out the following subsequent steps: step i), step ii), step iii) and step iv) on the extract enriched in large cell fragments; or step i), step ia), step ii), step iii) and step iv) on the extract enriched in large cell fragments.

A dried purified extract enriched in small cell fragments is obtained after carrying out the following subsequent steps: step i), step ii), step iii) step vi) on the extract enriched in small cell fragments, and step vi); or step i), step ia), step ii), step iii), step vi) on the extract enriched in small cell fragments and step vi).

A dried purified extract enriched in large cell fragments is obtained after carrying out the following subsequent steps: step i), step ii), step iii), step vi) on the extract enriched in large cell fragments and step vi); or step i), step ia), step ii), step iii), step vi) on the extract enriched in large cell fragments and step vi).

A mixed extract (a microbial cell product according to the invention) is obtained after carrying out the following subsequent steps: step i), step ii), step iii), and step v) of mixing (part of) the extract enriched in small cell fragments and (part of) the extract enriched in large cell fragments; or step i), step ia) step ii), step iii), and step v) of mixing (part of) the extract enriched in small cell fragments and (part of) the extract enriched in large cell fragments.

A dried mixed extract (a microbial cell product according to the invention) is obtained after carrying out the following subsequent steps: step i), step ii), step iii), step v) of mixing (part of) the extract enriched in small cell fragments and (part of) the extract enriched in large cell fragments and step vi); or step i), step ia), step ii), step iii), step v) of mixing (part of) the extract enriched in small cell fragments and (part of) the extract enriched in large cell fragments and step vi).

A mixed purified extract (a microbial cell product according to the invention) is obtained after carrying out the following subsequent steps: step i), step ii), step iii), step vi) on both extract enriched in small cell fragments and the extract enriched in large cell fragments and step v) of mixing (part of) the purified extract enriched in small cell fragments and (part of) the purified extract enriched in large cell fragments; or step i), step ia), step ii), step iii), step vi) on both extract enriched in small cell fragments and the extract enriched in large cell fragments and step v) of mixing (part of) the purified extract enriched in small cell fragments and (part of) the purified extract enriched in large cell fragments.

A dried mixed purified extract (a microbial cell product according to the invention) is obtained after carrying out the following subsequent steps: step i), step ii), step iii), step vi) on both extract enriched in small cell fragments and the extract enriched in large cell fragments, step v) of mixing (part of) the purified extract enriched in small cell fragments and (part of) the purified extract enriched in large cell fragments and step vi); or step i), step ia), step ii), step iii), step vi) on both extract enriched in small cell fragments and the extract enriched in large cell fragments, step v) of mixing (part of) the purified extract enriched in small cell fragments and (part of) the purified extract enriched in large cell fragments and step vi).

A mixed dried extract (a microbial cell product according to the invention) is obtained after carrying out the following subsequent steps: step i), step ii), step iii), step vi) on both the extract enriched in small cell fragments and the extract enriched in large cell fragments and step v) of mixing (part of) the dried extract enriched in small cell fragments and (part of) the dried extract enriched in large cell fragments; or step i), step ia), step ii), step iii), step vi) on both the extract enriched in small cell fragments and the extract enriched in large cell fragments and step v) of mixing (part of) the dried extract enriched in small cell fragments and (part of) the dried extract enriched in large cell fragments.

A mixed dried purified extract (a microbial cell product according to the invention) is obtained after carrying out the following subsequent steps: step i), step ii), step iii), step vi) on both extract enriched in small cell fragments and the extract enriched in large cell fragments, step vi) on both the purified extract enriched in small cell fragments and the extract enriched in large cell fragments extract and step v) of mixing (part of) the dried purified extract enriched in small cell fragments and (part of) the dried purified extract enriched in large cell fragments; or step i), step ia), step ii), step iii), step vi) on both extract enriched in small cell fragments and the extract enriched in large cell fragments, step vi) on both the purified extract enriched in small cell fragments and the purified extract enriched in large cell fragments and step v) of mixing (part of) the dried purified extract enriched in small cell fragments and (part of) the dried purified extract enriched in large cell fragments.

As shown in FIG. 1, different by-products may be obtained. This first and/or second by-product may be further processed by e.g. drying or concentration to obtain a dried or concentrated by-product.

Microbial biomass, which comprises microbial cells, has been used traditionally to produce a broad range of products of industrial interest, or have been used directly in a number of applications. Most industrial or commercial applications make use of a selected group of microbial biomass strains from the domains bacteria, yeast, fungi and algae. In overall terms, products obtained from microbial biomass are either intracellular or extracellular. Extracellular products are excreted by the cells into the bulk medium, usually an aqueous phase. Intracellular products, on the contrary, remain inside of the cells. In order to obtain intracellular products, additional processing is needed to release these products from the cells (by breaking the cell membrane or wall) and to further separate the compounds of interest from the remaining biomass and other impurities.

In the particular field of food applications, microbial biomasses have been used as a source of proteins (single cell protein—SCP), as nutritional supplements, or to produce various ingredients and additives.

Microbial biomasses are often used in the form of extracts, for which the microbial cells forming said biomass need to be disrupted/disintegrated. Extracts prepared from several different starting materials are known, such as fungal extract, algae extract and yeast extract. Of these extracts, the most commonly used is that derived from yeast, the so-called yeast extracts (hereinafter referred to as "YE"). YE are (and can be) applied in a broad range of products ranging from growth media for culturing cells for laboratories to nutritional supplements and flavor enhancers for the food industry. Production processes of YE are well-known. In general, yeast cells, mostly from the genus *Saccharomyces*, are disrupted (=disintegrated) by means of heat induced or chemically induced autolysis (or plasmolysis), followed by a step of incubation at high temperatures (>50° C.) in order to activate endogenous enzymes, which break down (=digest) the large intracellular products such as proteins and nucleic acids into smaller components thereof such as peptides, amino acids and nucleotides. The digested slurry that is obtained is then further purified and supplemented—depending on the final application—to provide an extract that can be commercialized as YE.

Generally, cell disintegration methods can be classified as being either non-mechanical or mechanical. Non-mechanical disintegration methods can be further sub classified into three categories: physical disintegration (e.g. by means of decompression, osmotic shock, thermolysis, ultrasonics, or freezing and thawing), chemical disintegration (e.g. by use of solvents, detergents, chaotropes, acids and bases, or chelates) and enzymatic disintegration (e.g. by autolysis, phage lysis, or lytic enzymes). The present invention is related only to mechanical disintegration methods. Examples of mechanical disintegration methods are ball mills, including bead mills, and homogenizers.

Homogenizers work under high-pressure and are in fact a positive-displacement pump that forces a cell suspension through a valve, before impacting the stream at high velocity on an impact ring. Often, several passes at high-pressure are required, which may lead to rising temperatures causing local denaturation of labile molecules.

Ball mills (including bead mills) can be either vertical and horizontal and use a grinding medium which is present in the grinding chamber. A motor drives a rotor to rotate the cell suspension at a high speed. The cell suspension and the grinding material (e.g. beads) generate shearing force to break the cells. This results in the release of intracellular materials into the aqueous suspension and will also result in cell fragmentation (i.e., disintegration). With increasing rotor speed, the shear force increases and the cell breakage increases. With decreasing grinding material size, the cell breakage usually increases. Other parameters affect the performance of the disintegration process. The skilled person is capable of selecting the right parameters and variables in accordance to the present invention.

Examples of cell disintegration methods according to the prior art are the following. U.S. Pat. No. 3,888,839A discloses a process for obtaining a protein isolate from yeast cells, wherein the yeast cells are ruptured by high-pressure homogenization (mechanical disintegration) and subsequent incubation. EP1199353A1 discloses a process for producing yeast extracts by treating yeast suspensions or yeast pastes and separating off the insoluble constituents, in which the yeast suspensions or yeast pastes are subjected to high-voltage electrical pulses (physical disintegration). EP2774993A1A discloses the use of a cell wall-decomposing enzyme (enzymatic disintegration) that does not contain protease and then heat-treating the product for 10 to 20 minutes at 70-80° C.

Microbial cells present in microbial biomass suspensions contain mostly proteins, carbohydrates, lipids and minerals. Proteins and other labile molecules experience unfolding, denaturation and degradation when exposed to high temperatures, long incubation times, extreme values of pH, solvents, salts and other harsh chemicals. When proteins and other functional molecules are denatured (tertiary and quaternary structure is lost), (part of) their functional activity is lost. Upon denaturation (unfolding), proteins lose their ability to interact with hydrophilic and hydrophobic surfaces, and also their ability to rearrange and form network-like structures upon heat-cooling treatments is affected. (Protein) functionality is of high importance in many commercial applications, in particular for applications in which the gelation properties—similar to those of egg-whites—are required. The present inventors have observed that the use of mechanical disintegration at the conditions described herein (for example, at the stated temperature and pH range) is sufficiently gentle to prevent unfolding, denaturation and/or degradation of proteins and other labile molecules, and therefore, necessary to preserve the functional properties, in particular gelation behavior.

In an embodiment, the mass concentration of microbial cells in said suspension of step i) is in the range of 1-25%, preferably of 5-15%. Mass concentration is the percentage of dry weight, 10% dry weight being the same as 100 g/L.

The aqueous suspension comprising microbial cells may further comprise cytoplasmic material or other extracellular material produced during propagation or fermentation.

In an embodiment of the method according to the present invention, the microbial cells are selected from unicellular or colonial prokaryotes and eukaryotes and one or more combinations thereof. In a preferred embodiment, the microbial cells are selected from the group consisting of yeast, algae, bacteria, fungi, and one or more combinations thereof. In a specific embodiment, the microbial cells are yeast.

In an embodiment, the method further includes after step i) and prior to step ii), ia) pretreating the aqueous suspension comprising microbial cells to obtain a pretreated aqueous suspension comprising microbial cells and a byproduct. In a specific embodiment, said pretreating is selected from decanting, centrifuging, filtering such as membrane filtering, and one or more combinations thereof. Prior to said pretreating the aqueous suspension comprising microbial cells may be washed. The combination of washing and then pretreating may be seen as a dual pretreatment. Washing can for instance be done with water, an acid or a base, or with solvents such as ethanol. In this embodiment, the order of steps is as follows: step i), step ia), step ii), wherein in step ii) of subjecting said suspension to mechanical cell disintegration the pretreated suspension obtained in step ia) is used.

In an embodiment, said mechanical cell disintegration of step ii) is performed using bead milling. In an embodiment, bead milling is used for a period of time in the range of 1 minute to 3 hours. Milling time can also be used to tune the amount of cytoplasmic compounds and other cell-derived compounds, such as proteins and carbohydrates, that are released into the aqueous suspension. The cell disintegration process may be carried out at 15-35° C. (preferably around 25° C.), to reduce metabolic activity, to preserve the functionality of proteins and to reduce cooling costs. The disintegration process is preferably carried out at pH 7-11, preferably around pH 9. Alternatively, the cell disintegration is conducted at T<25° C., for a period >3 h and at pH 11.

The disintegration conditions are preferably selected so as to provide a desired particle size distribution. As is discussed further herein, altering the particle size distribution may allow the final properties of the mixed product to be altered, for example to suit a particular intended use. The disintegration process is run in such a way that a bimodal particle size distribution (psd) is obtained, displaying a peak of intact cells, and a peak of cell fragments. For the case of yeast, a peak of intact cells ~6 um and a peak of cell fragments ~0.8 um is obtained. See FIG. 4 and FIG. 9.

During the course of the cell disintegration process, the psd varies, showing a decrease in the peak of intact cells, and a consequent increase in the peak of cell fragments. The disintegration process is run until a specific psd is obtained.

Figure 10A:
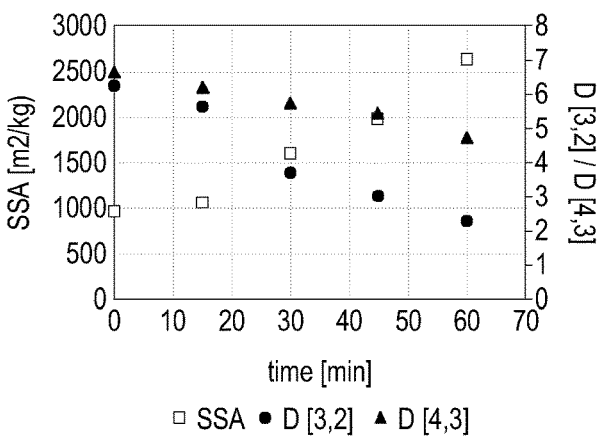
FIGS. 10A and 10B show specific surface area and particle size distribution for yeast over time during disruption.
Figure 10B:
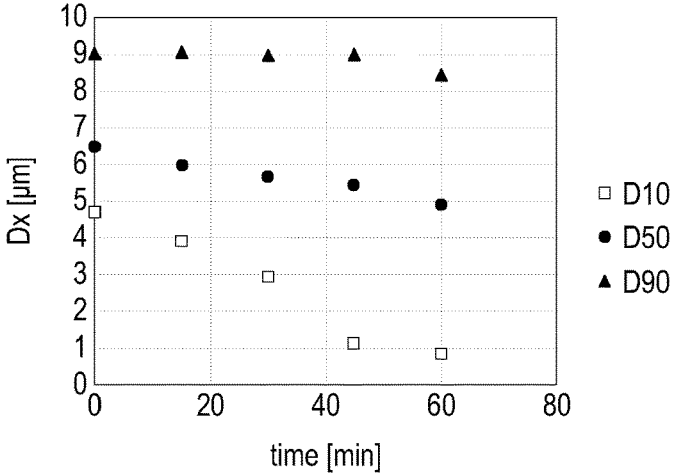

For the example case of yeast, the specific surface area increases over time, while the D[3,2], D[4,3], D10, D50, D90 decrease over time—See FIGS. 10A, 10B. For yeast, the desired target psd is D10<0.5 um, D50<4.5 um, D90<7.5 um and D[3,2]<2, D[4,3]<4.5. The skilled person is able to adjust the parameters of the specific disintegration method/equipment to reach the desired psd. This can be performed for example, with a bead mill, homogenizer or other equipment and specific settings, as extensively described in the specialized literature.

Bead sizes that may be considered are in the range of 0.1-5 mm, preferably in the range of 0.5-1 mm. Suitable bead materials include, but are not limited to, zirconium and glass.

Bead fillings (the percentage of the bead mill chamber that is filled with beads) that may be considered suitable are in the range of 40-90%, preferably in the range of 65-80%, based on the total available volume of the bead mill chamber.

Rotational speeds that may be considered suitable are in the range of 1-20 m/s. Depending on the configuration and geometry of each bead mill, the skilled person can estimate the corresponding rotor speeds in rpm. Suitable rotational speeds in rpm are for example 500-5000 rpm, preferentially 1000-3000 rpm.

Concentration of microbial cells that may be considered suitable are in the range of 2-25% dry weight.

In one specific embodiment, microbial cells are disintegrated using a Dyno-mill Research Lab (CB Mills) bead mill. Cells can also be disrupted by shear forces, such as with the use of blending (such as with a high speed or Waring blender as examples), the French press, or even centrifugation in case of weak cell walls, to disintegrate cells.

In an embodiment, cell disintegration takes place without the addition of chemicals and/or solvents.

In an embodiment, the pH value during step ii) is in the range of 4-11. In a preferred embodiment, the pH value during step ii) is in the range of 7.5-9.

In an embodiment, the temperature during step ii) is below 45° C., preferably equal to or below 35° C., such as below 35° C. or between 15 and 25° C.

In an embodiment, the disintegration step is carried out in such a manner that at least 10% of the particles have a size ≤1.5 um, and at least 50% of the cell fragments obtained have a size ≤4.5 um.

The method further includes after step ii) a step iii), step iii) being subjecting the aqueous suspension comprising disintegrated microbial cells obtained in step ii) to a separation treatment, to obtain an extract enriched in small cell fragments and an extract enriched in large cell fragments as microbial cell products, in addition to soluble compounds in which the extracts are suspended. In other words, the aqueous suspension comprising disintegrated microbial cells is separated into two extracts. These may be referred to herein as EESF (extract enriched in small fragments) and EELF (extract enriched in large fragments). The separation treatment may be a solid-liquid separation. Separation treatment may take place using any suitable method known to the skilled person. In a preferred embodiment, the separation treatment is selected from the group consisting decanting, centrifuging, filtering such as membrane filtering, and one or more combinations thereof. Suitable methods for separation further include settling, sedimentation, flocculation/coagulation, precipitation, decantation, (hydro)cyclonic separation and (air) flotation. The particular separation conditions may also be fine-tuned in order to obtain enriched extracts with particular preferred properties, as is explained herein.

The extract enriched in small cell fragments may comprise mostly soluble cytoplasmic material and small cell fragments, while the extract enriched in large cell fragments may comprises mostly large cell fragments and some soluble cytoplasmic material.

The EESF is preferentially obtained via centrifugal separation, at low and medium intensities. By low and medium intensities is meant either short times or low g forces, or combinations. An example of low intensities is separation for <2 min at <4000 rcf in a bench top centrifuge. An example of medium intensities is separation for <15 min at <4000 rcf in a bench top centrifuge. An example of high centrifugation intensities is >20 min at >20000 rcf.

Low and medium separation intensities are preferred in order to enhance the yields in the EESF. Furthermore, low and medium intensity separations lead to superior functionalities in the EESF.

In an embodiment, said separation treatment of step iii) is centrifuging at a centrifugal force equal to or smaller than 4000 relative centrifugal force (rfc).

In an embodiment, said centrifuging takes place for a period of time equal to or shorter than 20 min. In a specific embodiment, said centrifuging takes place for a period of time equal to or shorter than 15 minutes.

In an embodiment, said extract enriched in small cell fragments comprises microbial cell fragments and soluble cytoplasmic compounds, wherein at least d50≤500 nm.

In an embodiment, the extract enriched in small cell fragments comprises at least 1%, preferably at least 10%, such as at least 20% or even at least 30% or at least 50%, more small cell fragments than the aqueous suspension depleted in small cell fragments (viz. the extract enriched in large cell fragments) obtained at the same time.

The separation parameters may be adjusted to obtain preferential recovery of a preferred particle size distribution. For example, in the case of yeast, preferential recovery of particles in the range 0.1-3 um for the EESF (at least d50≤500 nm) and particles in the range 3-10 um for the EELF may be targeted.

The particle size distribution of the EESF varies as result of the separation intensity in a centrifugal separator.

In certain embodiments, the water content of the disintegrated cell preparation may be adjusted prior to the separation step. Altering the dilution levels can modify the functional properties of the EESF and EELF.

In an embodiment, the method further comprises incubating the EESF prior to the mixing step v). It has been found that during the course of cell disintegration, the pH decreases (for example, from ~9 to ~6.5). Under these conditions, substantial $CO_2$ release may take place. This provides a leavening effect that can be used in several food applications. However, this may not always be desirable, and so the EESF can be subjected to an incubation step in order to deplete the excess $CO_2$. For example, the EESF may be incubated at below 25° C. for at least 60 minutes, under gentle or no stirring and under aerobic conditions. In an embodiment, the EESF, as a liquid suspension containing >5% DW, is left under stirring for a period >60 min and T<25° C. During the incubation process the excess gas is released without compromising the functional properties of the EESF. After the incubation process, the leavening effect is drastically reduced. Furthermore, to the surprise of the inventors, the leavening effect can be substantially diminished if the pH is slightly raised, for example from pH<6.5 after disintegration to pH>6.9, for example pH 6.9 or pH 7.0.

In an embodiment, the method further includes iv) subjecting at least one of the microbial products obtained in step ii) or step iii) to a purification treatment, to obtain at least one purified microbial cell product. Purification treatment may take place using any suitable method known to the skilled person. Examples of purification methods are adsorption, chromatography, filtration such as diafiltration or membrane filtration, crystallization, flocculation/coagulation, precipitation, two-phase extraction, sub-critical and supercritical extractions, and solvent extraction. In a preferred embodiment, the purification treatment is from the group consisting of washing, filtering such as membrane filtering or diafiltration, adsorption, chromatography, crystallization, flocculation/coagulation, precipitation, two-phase extraction, sub-critical and supercritical extractions, solvent extraction, and one or more combinations thereof. In case both of the microbial products obtained in step ii) are step iii) are subjected to a purification treatment, these purification treatments are independently selected.

In an embodiment, said purification treatment of step iv) is membrane filtration, wherein the cut-off value of the membrane used is in the range of 1 kDa to 20000 kDa, preferably in the range 10 kDa to 1000 kDa. In an embodiment, the cut-off value of the membrane used is in the range of 0.1-2 μm.

The method includes v) mixing at least part of the extract enriched in small cell fragments obtained in step iii) and at least part of the extract enriched in large cell fragments obtained in step iii) to obtain a mixed extract as microbial cell product or mixing at least part of a purified extract enriched in small cell fragments obtained in step iv) and at least part of a purified extract enriched in large cell fragments obtained in step iv) to obtain a mixed purified extract as microbial cell product. This mixing can be used to further tune the product. For instance, mixing may be applied when it appears that the separation has been too 'thorough' for the intended purpose, i.e. the enrichment of the extracts was too high. For example, when the amount of small cell fragments in the extract enriched in small cell fragments is higher than optimal for a certain purpose, a part of the extract enriched in large cell fragments can be mixed with the extract enriched in small cell fragments to obtain a mixed extract.

It is important to note that this provides a mixed product with different characteristics from either the EESF or the EELF, and additionally with different characteristics from a disintegrated cell preparation since at least some soluble components are removed during the separation step. As will be apparent from the details provided herein, the specific EESF and EELF extracts can be produced in slightly different ways under slightly different conditions, in order to obtain desired properties, and then the proportions to be combined may also be varied to obtain desired properties in the mixed product.

In an embodiment, the method further includes vi) subjecting at least one of the microbial products obtained in step ii), step iii), step iv) or step v) to drying, to obtain a dried microbial cell product. In a preferred embodiment, drying is with a method selected from spray drying, freeze drying and fluidized bed drying. Drying may also be concentrating. Preferably, the dried microbial cell product has a moisture content of 10 wt. % or less, more preferably or 5 wt. % or less, based on the total weight of the dried microbial cell product. Spray drying and fluidized bed drying, conducted above 150° C. and below 200° C., lead to a product with a neutral color, aroma and taste. This is due to the elimination of volatile compounds during drying. Freeze drying is a preferred technology to preserve aroma, color and taste, as those are preserved during sublimation.

Concentration is preferred in order to further preserve the functional properties of the EESF and EELF. Concentration is preferably conducted with methods known in the art where the product is not exposed to temperatures >50° C. or <0° C. An example of such method is membrane concentration. The EESF and EELF is preferentially concentrated to reach a DW content >20%.

In an embodiment, the method further includes vii) mixing at least part of a dried extract enriched in small cell fragments obtained in step vi) and at least part of a dried extract enriched in large cell fragments obtained in step vi) to obtain a mixed dried extract as microbial cell product or mixing at least part of a dried purified extract enriched in small cell fragments obtained in step vi) and at least part of a dried purified extract enriched in large cell fragments obtained in step vi) to obtain a mixed dried purified extract as microbial cell product. It is also possible that one of the dried extracts is purified, and one of the dried extracts is not purified before mixing. For simplicity, this option is not depicted in FIG. 1.

All the mixing strategies described in FIG. 1 are also applicable when the EESF and the EELF are concentrated instead of dried. For simplicity, this option is not depicted in FIG. 1.

In an aspect, the invention relates to an extract enriched in small cell fragments obtainable by the method including at least steps i), ii) and iii) as described above, wherein the extract comprises soluble proteins having a molecular weight above 10 kDa, preferably above 50 kDa, more preferably above 60 kD, in their native conformation. In an embodiment, at least 95% of all soluble proteins in said extract have a molecular weight above 10 kDa, preferably above 50 kDa, more preferably above 60 kD, in their native conformation.

In an embodiment of this aspect, said extract enriched in small cell fragments comprises microbial cell fragments and soluble cytoplasmic compounds, wherein at least 80% said cell fragments have a d50≤500 nm.

In an embodiment of this aspect, the extract enriched in small cell fragments comprises at least 1%, preferably at least 10%, such as at least 20% or even at least 30% or at least 50%, more small cell fragments that the aqueous suspension depleted in small cell fragments (viz. the extract enriched in large cell fragments) obtained at the same time.

In an embodiment, the microbial cell product provides binding, moisturizing, water-oil-holding, and/or emulsifying properties similar to an egg. In some cases, the microbial cell products are used as a binding agent. In some cases, the microbial cell products are used as a moisturizing agent. In some cases, the microbial cell products are used as an emulsifying agent. In some cases, the microbial cell products are used as a foaming agent. In some cases, the microbial cell products are used as a water or oil-holding agent. In some cases, the microbial cell products are used as a gelation agent.

In some embodiments, the microbial cell products can be used as a substitute for egg yolks, egg whites, or whole eggs in the preparation of an equivalent product prepared using an equivalent or inequivalent amounts of eggs. In a preferred embodiment, the microbial cell product is used as a substitute for egg whites.

In some aspects, the invention provides a food product comprising the mixed microbial cell product as described herein.

In an embodiment, the pH value during step iii) and/or step iv) is comparable as at the end of step ii) of the method. In an embodiment, the temperature during step iii) and/or step iv) is the same as during step ii) of the method.

Although primarily described herein with reference to preparations obtained from yeast cells, the invention is not limited to the same. Various other microorganisms can be used. In embodiments, the microbe may be selected from fungi, including yeast (preferably *Saccharomyces* sp, more preferably brewer's or baker's yeast); plants, in particular microalgae (including *Tetraselmis* sp or *Chlorella* sp, for example *C. vulgaris*); and cyanobacteria (including *Arthrospira* sp, preferably *A. platensis*). The microbe may also be selected from bacteria, for example lactic acid bacteria.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The scope of the present invention is defined by the appended claims. One or more of the objects of the invention are achieved by the appended claims.

METHODS

Providing Aqueous Suspension Comprising Microbial Cells

In an example of providing an aqueous suspension, the aqueous suspension is prepared by adding a Baker's yeast (either dry or as a wet suspension) to a known volume of water under gentle stirring and constant temperature, to reach a concentration of 100 g/L (10% dry weight). Stirring is conducted until an homogenous suspension is achieved.

pH Adjustment

Adjustment of the pH is done, as an example, by adding slowly a 5M NaOH solution to the aqueous suspension comprising microbial cells, under constant gentle stirring and constant temperature, until the desired pH is achieved. Other solutions of NaOH, and other types of base (e.g., $CaOH_2$) can be used to adjust the pH of the microbial suspension. Similarly, solutions of suitable acids can be used to decrease the pH of the microbial suspension.

Pre-Treatment

In an example, pretreatment of the microbial biomass can be performed by washing, which comprise four steps:
1) An homogenous yeast suspension (100 g/L) is subjected to centrifugation at 3000 rcf for 5 min and at a temperature of 15° C.
2) The resulting supernatant is removed and replaced by an equivalent amount of water.
3) The obtained suspension is mixed gently until an homogeneous suspension was achieved.
4) Steps 1-3 are repeated 2-3 times. The removed supernatants can be collected separately or can be blended to give a byproduct (byproduct 1 in the present invention)

5) Steps 1-4 may be performed by the skilled person using process configurations known in the art. One example of such configurations is counter-current or co-current washing.

Cell Disintegration

In an example of cell disintegration of yeast, Cell disintegration is performed using bead milling. This bead milling is conducted with a Dyno Mill research lab (Willy A. Bachofen AG). A 200 ml solution containing 100 g/L (10% DW) *Saccharomyces cerevisiae* at pH 8.9 is processed under batch recirculation mode during 15 min. A constant speed of 2039 rpm is used and the temperature is controlled in the range 24-26° C. The mill contains 0.5 mm spherical Zirconium beads at a 65% filling percentage. An aqueous suspension comprising disintegrated microbial cells is therefore obtained.

Separation Treatment

In an example of separation, separation is done by centrifugation, conducted in a bench-top centrifuge Allegra X-22R, equipped with swinging buckets. Samples are centrifuged for 15 min and 4000 rcf at a temperature of 15° C. An extract enriched in small cell fragments is obtained as well as the residue being an aqueous suspension partly depleted from small cell fragments, also called an extract enriched in large cell fragments.

Purification Treatment

In an example of purification, purification is done by filtration, conducted with a lab scale TTF-system (Millipore). Filtration is conducted under a constant transmembrane pressure of <1 bar and under recirculation mode to achieve a 3-6× concentration factor. For each trial, a 1× dilution, with water, is applied before each filtration round. Therefore, the purification is also conducted as a diafiltration process.

Purification is done by ultrafiltration or microfiltration, viz. using either an ultrafilter or microfilter in the above method. Ultrafiltration is conducted using hydrophilic membrane cassettes in the range 10 kDa to 1000 kDa (Biomax). Microfiltration is conducted with a 0.2 μm hollow fiber membrane unit (GE).

Drying

In an example of drying, drying is conducted with a spray dryer (Ollital Technology) at 180° C. to reach a final moisture content of <5 wt. %. Drying can also be performed with a freeze dryer (Zirbuss Gmbh 2×3×3) at −20° C. and <1 mbar for 48 h.

EXAMPLES

The present invention is further elucidated based on the Examples below which are illustrative only and not considered limiting to the present invention.

Example 1

An aqueous suspension comprising microbial cells from Baker's yeast is prepared as discussed above. The pH of the aqueous suspension is adjusted to pH 7 prior to cell disintegration.

Cell disintegration is applied as discussed above, and an aqueous suspension comprising disintegrated microbial cells is obtained.

Example 2

An aqueous suspension comprising microbial cells from Baker's yeast is prepared as described above. The pH of the aqueous suspension is adjusted to pH 7 prior to cell disintegration.

Cell disintegration and subsequent separation as discussed above are applied, and an extract enriched in small cell fragments and an extract enriched in large cell fragments are obtained.

Example 3

An aqueous suspension comprising microbial cells from Baker's yeast is prepared as discussed above. The pH of the aqueous suspension is adjusted to pH 9 prior to cell disintegration.

Cell disintegration, subsequent separation, and subsequent purification by ultrafiltration—as discussed above—of the extract enriched in small cell fragments are applied, and a purified extract enriched in small cell fragments is obtained.

Example 4

An aqueous suspension comprising microbial cells from Baker's yeast is prepared as discussed above. The pH of the aqueous suspension is adjusted to pH 9 prior to cell disintegration.

Cell disintegration, subsequent separation, and subsequent purification by microfiltration—as discussed above—of the extract enriched in small cell fragments are applied, and a purified extract enriched in small cell fragments is obtained.

Example 5

An aqueous suspension comprising microbial cells from Baker's yeast is prepared as discussed above. The pH of the aqueous suspension is adjusted to pH 9 prior to cell disintegration.

Cell disintegration, subsequent separation, subsequent purification by ultrafiltration—as discussed above—of the extract enriched in small cell fragments, and subsequent drying are applied, and a dried purified extract enriched in small cell fragments is obtained.

Example of Temperature and pH Variations in Different Steps

Table 1 shows an example of the pH and temperature throughout different process steps according to the present method.

| | Aqueous suspension comprising microbial cells | After pre-treatment | After pH adjustment | After bead milling | After ultra-filtration |
|---|---|---|---|---|---|
| pH | 5.8 | 6.5 | 8.9 | 7.1 | 7 |
| T [° C.] | 25 | 20 | 20 | 23 | 22 |

Effect of Processing Temperature During Bead Milling

The temperature during bead milling influences the gelation behavior of the obtained microbial cell product.

This was investigated by repeating Example 1, except for the temperature, which was varied in the range 20-55° C. An additional experiment was conducted (*) where disintegration was conducted without temperature control for a prolonged time of 1 h. A maximum temperature of 60° C. was recorded. The results are shown in Table 2.

The temperature was adjusted to the desired value before bead milling. The corresponding effect of temperature on cell disintegration was estimated using a flow cytometer (BD Accuri C6). Before measurement, samples were diluted 80 times in water and analyzed using the flow cytometer. Cell disintegration was determined from forward scattering data. The fraction of disrupted cells was estimated using the biomass suspension at T=20° C. as reference.

For all samples, the resulting extract enriched in small cell fragments was collected, dried and analyzed to determine the gelation performance.

Gelation was determined as follows. A solution containing 200 g/L (20% DW) in water was prepared. Further dilutions were made, in water, to reach 150 g/L (15% DW) and 100 g/L (10% DW). The suspensions were heated at 95° C. for 10 min using a block heater, and then cooled down to ambient temperature in a bath of water (T=25° C.). The resulting material was analyzed for their gelling characteristics according to the following ranking (scores): 0 means that no gelation was observed, 1 means that a paste was observed, 2 means that a tick paste was observed, 3 means that a very soft gel was observed, 4 means that a soft gel was observed, 5 means that a hard gel was observed.

TABLE 2

Gelation performance of extracts enriched in small cell fragments produced at different temperatures during bead milling.

| Temperature | Fraction intact | Gelation score | | |
|---|---|---|---|---|
| (° C.) | cells t = 0 | 20% DW | 15% DW | 10% DW |
| 20 | 1 | 5 | 4 | 2 |
| 25 | 1 | 5 | 4 | 2 |
| 35 | 1 | 5 | 4 | 0 |
| 45 | 0.9 | 5 | 4 | 0 |
| 55 | 0.8 | 4 | 2 | 0 |
| 60* | 1 | 0 | 0 | 0 |

Effect of pH on Protein Conformation and Protein Solubility at Different pH Values Example 2 was repeated, but the pH of the suspension was adjusted to different values of pH of the suspension prior to bead milling. The extract enriched in small cell fragments was taken and analyzed as follows:

Native gel electrophoresis: samples were loaded into pre-casted gels with 4-12% crosslinks, using 10× tris-glycine buffer as running buffer. Samples were run at 125V for 70 min and compared with a native protein marker. Protein bands were stained with Coomassie blue.

Protein solubility: protein concentration in the extract enriched in small cell fragments was measured in a spectrophotometer at 280 nm, as an indication of protein content. Data was normalized for easier interpretation.

Figure 2A:
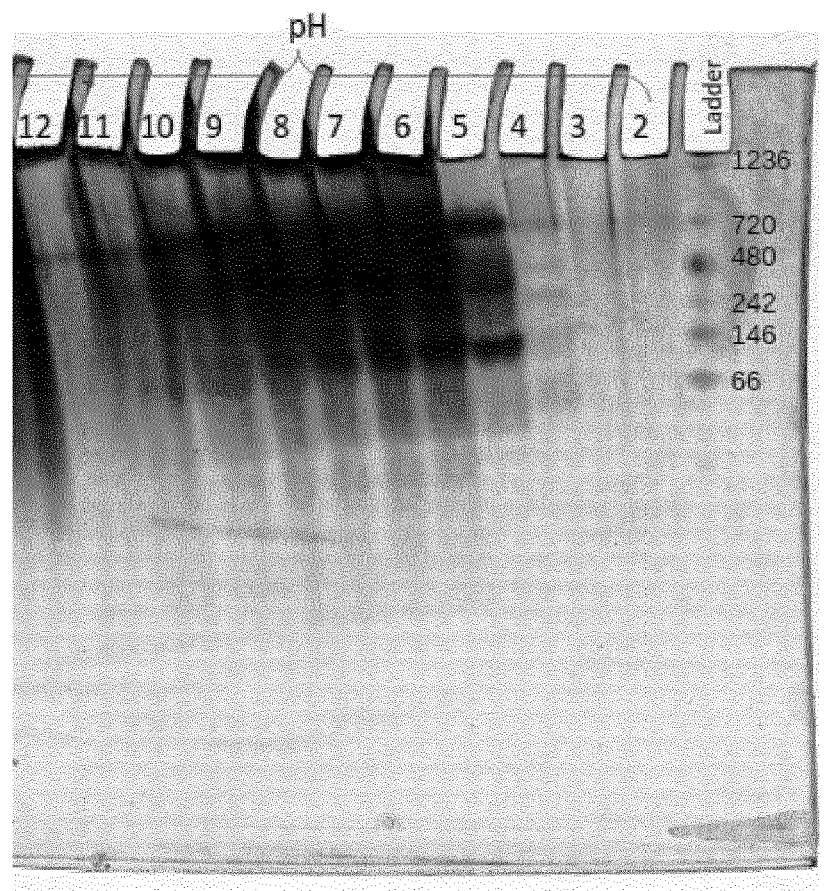
FIG. 2 shows profiles of proteins in their native conformation for extracts enriched in small cell fragments obtained under different pH values (left), and the solubility of proteins in the extract enriched in small cell fragments at different pH values (right).
Figure 2B:
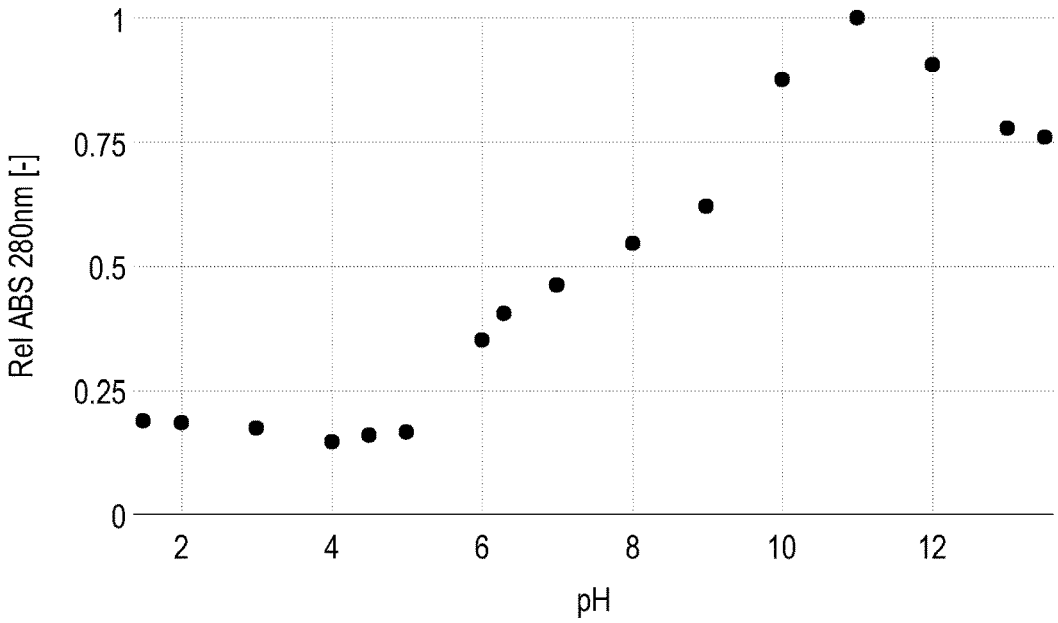

From FIG. 2B it becomes clear that the solubility of proteins present in the extract enriched in small cell fragments is higher for alkaline pH values. From FIG. 2A it can be seen that this increased solubility at alkaline pH values, especially in the range of 4 to 11 (preferably 7 to 9), is without affecting the native conformation of the proteins and other molecular complexes. FIG. 2A is a native gel electrophoresis showing bands if proteins are present in their native conformation. If a protein is denatured, then the corresponding band will disappear completely or will result in new bands at different molecular weights.

Effect of the Residence Time in a Bead Mill

Example 2 was repeated, and samples were taken at different time points during bead milling for further analysis. The extract enriched in small cell fragments was collected for further analysis.

Proteins were determined according to the method of Lowry (publication Lowry, O. H.; Rosebrough, N. J.; Farr, A. L.; Randall, R. J. (1951). "Protein measurement with the Folin phenol reagent". Journal of Biological Chemistry. 193 (1): 265-75), using BSA as standard protein. Carbohydrates were determined according to the method of Dubois (publication MICHEL DUBOIS, K. A. GILLES, J. K. HAMILTON, P. A. REBERS, and FRED SMITH. Colorimetric Method for Determination of Sugars and Related Substances. ANALYTICAL CHEMISTRY. VOLUME 28, NO. 3, March 1956), using glucose as standard sugar.

Figure 3:
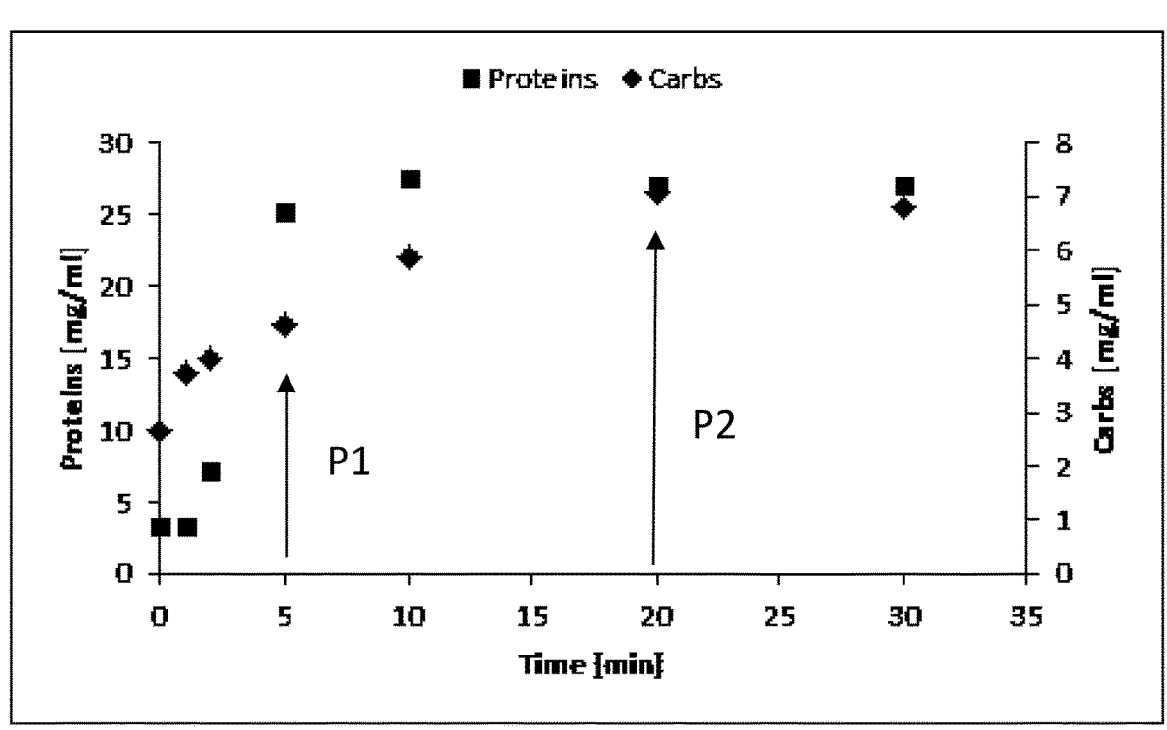
FIG. 3 shows the solubilization of proteins and carbohydrates in the extract enriched in small cell fragments during the course of a bead milling trial.

FIG. 3 shows a plot of the amount of solubilization of proteins (left vertical axis) and carbohydrates (right vertical axis) as a function of the residence time in the bead mill (horizontal axis). FIG. 3 shows how the residence time in bead milling influences the solubilization of proteins and carbohydrates. Since the rates of solubilization of individual molecules is different, the shear forces and the residence time in a bead mill can be adjusted in order to obtain extracts of different composition and therefore different functional activity.

This shows that by adjusting the residence time during the step of disintegration, control is obtained in view of the level of solubilization of proteins and carbohydrates. FIG. 3 provides an example on how choosing two different residence times can lead to two extracts with significantly different compositions. When the residence time is 5 minutes (see arrow at P1) it was found that the extract obtained contained 30% less soluble carbohydrates compared to a residence time of 20 minutes (see arrow at P2). Furthermore, the particle size distribution can also be adjusted as function of the residence time. This is of particular importance in the present invention, as the functional properties of final products depend on the particle size distributions.

Particle Size Distribution of Cell Fractions After Bead Milling

Example 2 was repeated, but different values for the milling time (residence time in bead mill) were used. The aqueous suspension comprising disintegrated microbial cells obtained (also called slurry) was collected for analysis. The extract enriched in small cell fragments obtained after subsequent separation was also collected for further analysis.

The particle size distribution was measured using a Zeta-Sizer Ultra (Malvern Panalytical) with disposable folded capillary cells. Samples are prepared in water to reach a concentration <10 g/L (1% DW). Samples are added to the measuring cell making sure no bubbles are formed. Samples are measured three times, with 30 s waiting time, at 25° C. and with a refractive index of 1.33.

The values for D99, D70 and D50 were calculated from particle size distribution data. The particle size for D99 indicates that 99% of the particles are larger than this value. The particle size for D70 indicates that 70% of the particles are larger than this value, and mutatis mutandis for D70 (70%) and D50 (50%). The percentage of particles of each size category was determined from the total count of particles, and the corresponding sizes per interval were estimated. Table 3 shows the ranges of particles after disintegration and after separation treatment.

TABLE 3

Values of D99, D70 and D50 for disintegrated microbial biomass suspensions (after disintegration) and extracts enriched in small particles (after separation).

|  | 15 min after disintegration | 15 min after separation | 3 h after disintegration | 3 h after separation |
|---|---|---|---|---|
| D99 (nm) | 92.9 | 32.3 | 79.9 | 68.7 |
| D70 (nm) | 488.7 | 169.9 | 197.6 | 361.3 |
| D50 (nm) | 660.3 | 361.3 | 361.3 | 488.7 |

Figure 4:
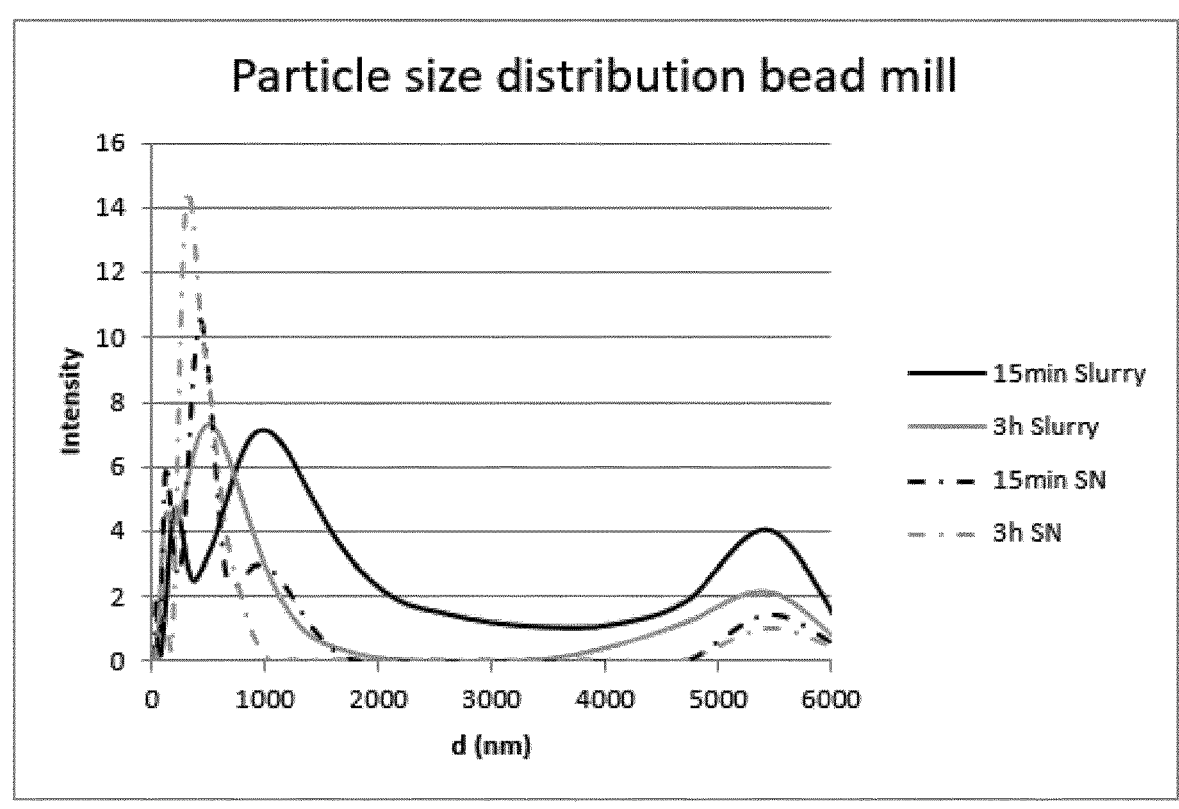
FIG. 4 shows the particle size distribution of cell fractions after bead milling or after bead milling and after separation by centrifugation.

FIG. 4 shows the particle size distribution of cell fractions in the aqueous suspension comprising disintegrated cells after bead milling for 15 min ('15 min Slurry'—solid black line). and 3 h ('3 h Slurry'—solid grey line). The horizontal axis shows the diameter of the cell fragments in nanometer and the vertical axis shows the intensity of the signal. These solid lines show a peak in the range of 200-400 nm (small cell fragments) as well as peaks in the area between 500 and 1500 nm and around 5500 nm. Additionally, the particle size distribution was determined after separation (centrifugation at 4000 rcf) for the extract enriched in small cell fragments (15 min SN and 3 h SN; wherein SN=supernatant). As demonstrated in FIG. 4, the result of said separation treatment is that the population of cell fragments with average size in the range 200-400 nm is selectively maintained using centrifugation methods, in other words these small cell fragments pass into the extract whereas the larger cell fragments remain in the initial disrupted suspension (or aqueous suspension depleted of small cell fragments or extract enriched in large cell fragments). This clearly shows the effect of the separation step of the present invention. To the surprise of the inventors, such small cell fragments (and hence the extract enriched in small cell fragments) display functional properties comparable to that assigned in the literature to highly pure ingredients, such as protein isolates.

The present invention often refers to a particle size of 500 nm for the extract enriched in small fragment. For the purpose of clarity and simplicity, this value refers to the d50.

One important element of the present invention is the fact that the extract enriched in small fragments, and the extract enriched in large fragments, present a multimodal distribution. Therefore, further characterization of the extracts and products—described above—was conducted using a Mastersizer 2000 (Malvern Panalytical), using a refractive index of 1.33 for the dispersant (water) and—for the case of yeast—a particle refractive index of 1.34. All analysis were conducted using the Mie scattering model.

Effect of the Centrifugal Field Force

Example 2 was repeated, but different values were used for the centrifugal force during the separation step. The resulting extract enriched in small cell fragments was collected for further analysis.

Maximum gelation strength (G' [Pa]) was measured with a rheometer (Anthon Parr). Samples were subjected to a heating-cooling treatment (25° C., then 90° C., then 25° C.). The value of G' max (also called storage modulus) was obtained at the end of the cooling step (at a temperature of about 28° C.).

Figure 5:
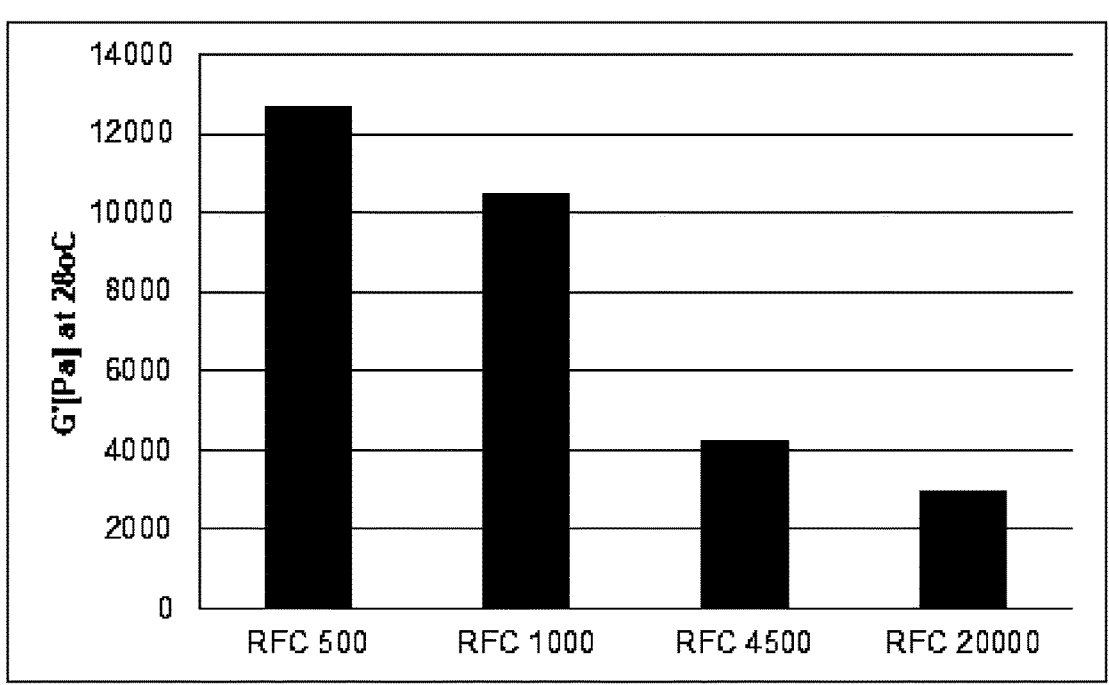
FIG. 5 shows the effect of the centrifugal field force on the maximum gel strength [Pa] after purification treatment.

FIG. 5 shows bars for several centrifugal field forces (RFC) and the effect thereof on the maximum gel strength. As shown in FIG. 5, the inventors have inventively found that adjusting the centrifugal forces has a direct effect on the functional properties of the resulting extracts of a separation treatment. Using low centrifugal forces leads to better gelling properties of the extract enriched in small cell fragments (supernatant). The skilled person is able to adjust the specific values of the centrifugal field forces and the time needed to achieve the desired solid-liquid separation, while keeping a population of cell fragments in the range 200-400 nm based on the invention disclosed herein. In the example given in FIG. 5 a centrifugal force <4000 rfc, for a time <15 min, is preferred.

Effect of Membrane Cut-Off on the Gelling Behavior of the Extract Enriched in Small Cell Fragments Example 3 was repeated, but different values for the membrane cut-off value for the filters used during purification were used.

The resulting purified extract enriched in small fragments was collected for further analysis.

Maximum gelation strength (G' [Pa]) was measured with a rheometer (Anthon Parr). Samples were subjected to a heating-cooling treatment (25° C., then 90° C., then 25° C.). The value of G' max [Pa] was obtained at the end of the cooling step (at a temperature of about 28° C.).

Figure 6:
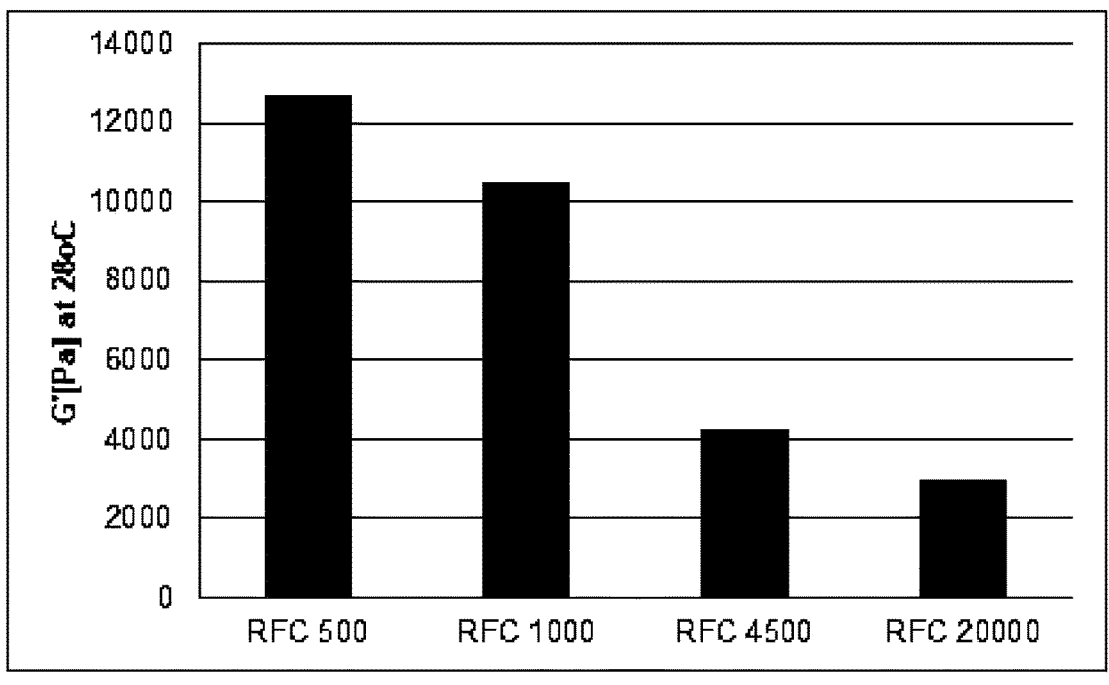
FIG. 6 shows effect of membrane cut-off on the gelling behavior of the purified extract enriched in small cell fragments, as measured by the gel strength G' max [Pa].

FIG. 6 shows bars of the purified extract enriched in small cell fragments according to the invention, compared to other protein rich sources such as egg white protein isolate, whey protein isolate and pea protein isolate, as measured by the gel strength. FIG. 6 shows that a membrane-based filtration can be applied as purification treatment to significantly enhance the gelling properties of the extract enriched in small cell fragments. The numbers 0.2, 100 and 10 represent the membrane cut-off value, i.e. 2 μm, 100 kDa and 10 kDa. In particular, a membrane-based filtration can be used to purify the extract enriched in small cell fragments into a retentate phase (purified extract enriched in small cell fragments) and a permeate phase (byproduct). FIG. 6 also shows as comparison extracts enriched in small cell fragments which have been disintegrated at pH 7 (enriched fraction pH 7) or pH 9 (enriched fraction pH 9). The purified extract enriched in small cell fragments (retentate fraction) exhibits good gelling properties, as demonstrated in FIG. 6. In addition, the extracts enriched in small cell fragments also show gelling properties, in particular the one at pH 9.

Surface Tension

Example 3 was repeated, but different values for the membrane cut-off value for the filters used during purification were used. The resulting byproduct and purified extract enriched in small fragments was collected for further analysis as follows.

Surface tension was measured using an automated drop tensiometer (ADT, Teclis Tracker). Air-water and hexadecane-water (oil-water) were used as reference samples.

Figure 7:
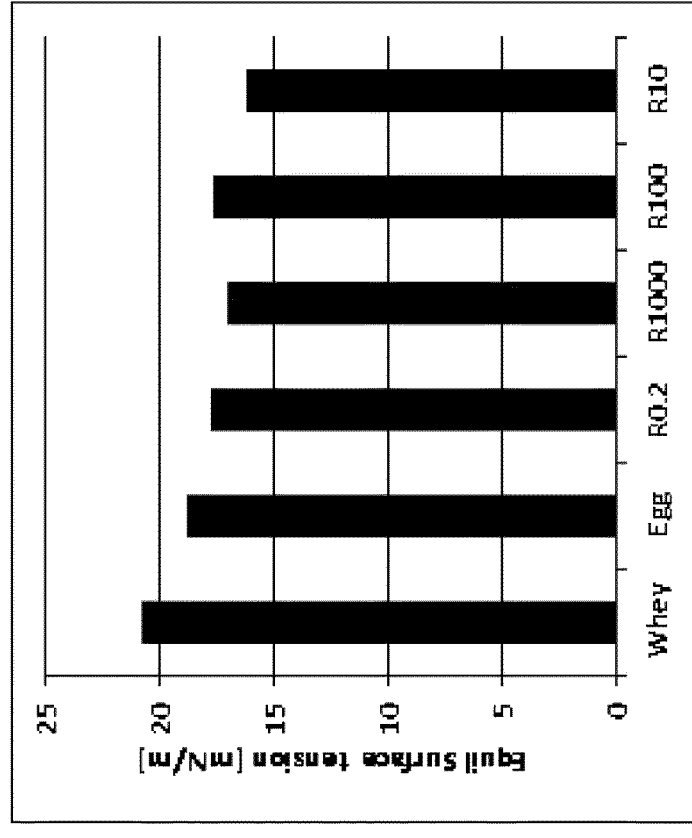
FIG. 7 shows the equilibrium surface tension of an obtained byproduct (P, left figure) and the purified extract enriched in small cell fragments (R, right figure) on air-water (left) and oil-water (right) interfaces compared to the surface tension of egg white protein isolate and whey protein isolate.
Figure 7:
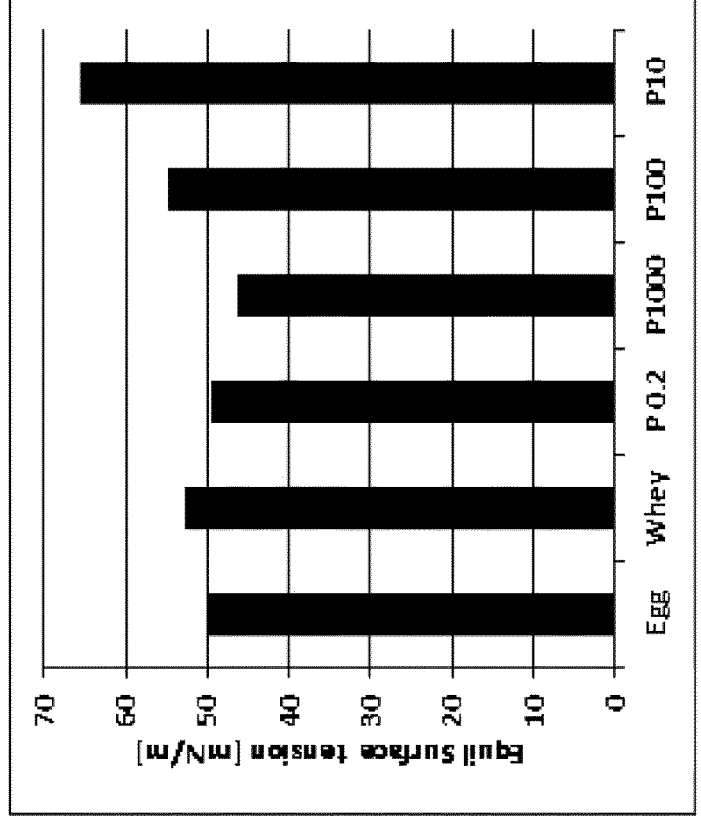

FIG. 7 shows bars with the equilibrium surface tension on obtained byproduct (P) on an air-water interface (left) and on purified extract enriched in small cell fragments (R) on an oil-water interface (right). The values for egg-white protein isolate and whey protein isolate are used as comparison. The equilibrium surface tension reflects the extent of surface stability; lower values are obtained from samples with superior activity. The numbers 0.2, 1000, 100 and 10 represent the membrane cut-off value, i.e. 2 μm, 1000 kDa, 100 kDa and 10 kDa used in filtration during the purification step. The purification treatment according to some embodiments of the present invention provides a way to selectively fractionate the extract enriched in small cell fragments into a purified extract enriched in small cell fragments and a byproduct. Both of these extracts exhibit, in addition to gelling behavior, excellent surface activity, as shown in FIG. 7. The inventors discovered that such surface activity is also reflected in the foaming and emulsification activity of the extracts according to the present invention, which are comparable or superior to typical protein isolates.

Example Composition of Extracts

Example 3 was performed, and the resulting extracts were further analyzed.

The extracts enriched in small cell fragments and large cell fragments obtained after a separation treatment may be rich in proteins and carbohydrates. Table 4 presents an example composition of an extract enriched in small cell fragments and an extract enriched in large cell fragments. In the table, "ash" refers to any inorganic material, such as minerals.

TABLE 4

Example composition of extracts in DW %

| | Extract enriched in small cell fragments | Extract enriched in large cell fragments |
|---|---|---|
| Proteins | 57% | 43% |
| Carbohydrates | 22% | 37% |
| Ash | 13% | 14% |
| Lipids | 8% | 6% |

Further Investigations

Figure 9:
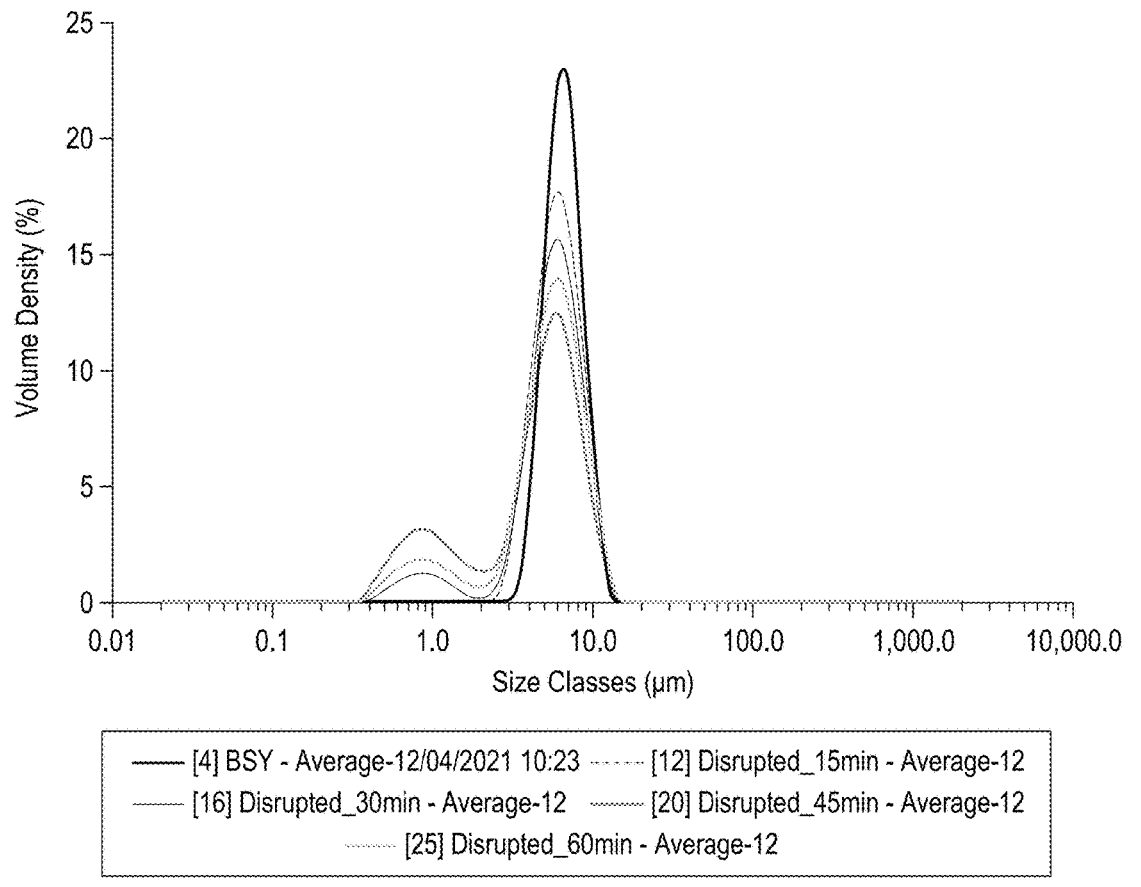
FIG. 9 shows a particle size distribution for yeast under different disruption conditions.

Further investigations were carried out regarding the effect of different processing and preparation methods on the properties of microbial preparations. As can be seen in FIG. 9, the particle size distribution varies as the disintegration process is run over longer times. In the case of yeast, a peak of intact cells ~6 um and a peak of cell fragments ~0.8 um is obtained, with the intact cell peak decreasing and the cell fragment peak increasing as disruption time is increased. The disintegration process can therefore be run until a desired particle size distribution is obtained. For yeast, the desired target psd is D10<0.5 um, D50<4.5 um, D90<7.5 um and D[3,2]<2, D[4,3]<4.5. FIG. 10 shows the various measurements over time.

Figure 11:
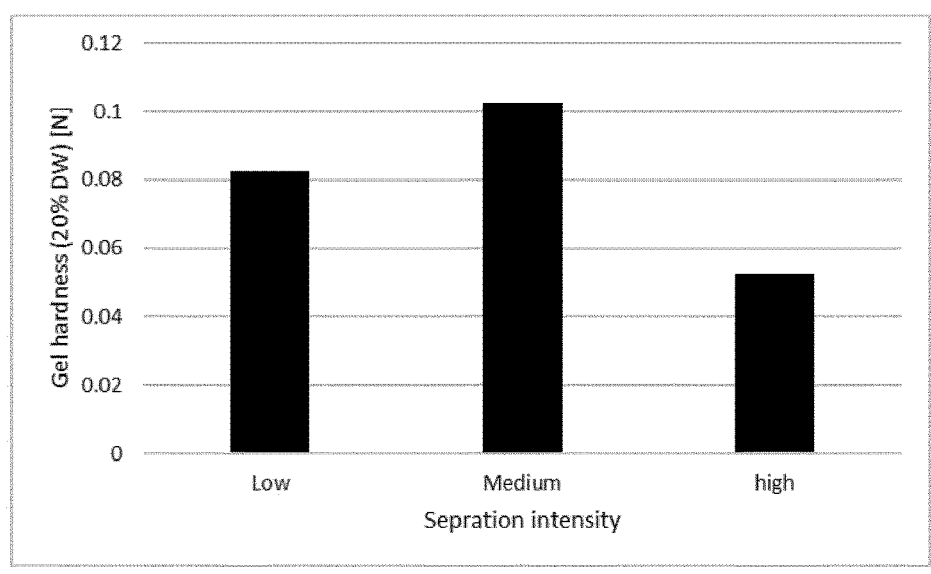
FIG. 11 shows gel hardness of a microbial cell product under low, medium, and high separation intensities.

The effect of varying separation conditions is shown in FIGS. 11-13. For these examples, the disrupted yeast preparation was separated by centrifugation under low, medium, and high intensity. Low and medium intensity can improve yield in the EESF. As an example, >10% yields (DW) for the EESF can be obtained using low and medium centrifugation intensities vs high centrifugation intensities.

Further, at high intensity, the gel forming properties of the EESF are reduced, while low and medium intensity give improved gel forming properties (FIG. 11). Using high intensity separations lead to inferior functionality in the EESF. Medium separation intensities are preferred to ensure superior functionality in the EESF. By "functionality" in this context is meant gelation hardness—as an example, at low intensity separation a gel hardness of 0.08-0.1 N is obtained, while at high intensity separations a gel hardness of N is obtained.

It is thought that the different separation intensities alter the particle content of the EESF or EELF; see FIGS. 12 and 13. By increasing the separation intensity, the specific surface area increases, but the number of particles decreases substantially. It is preferred to use low separation intensities in order to enrich the EESF with particles in the range 0.1-3 um. At high intensity separation conditions, mainly soluble compounds remain in the liquid phase with a small quantity of particles in the range 0.1-0.3 um. See FIG. 12. By increasing the separation intensity, the specific surface area increases, but the number of particles decreases substantially. See FIG. 13. These particles are essential in order to enhance overall yields and functional properties in the EESF; hence a balance between low and high separation intensity must be found.

The EELF preferentially contains fragments in the range 2-10 um. Cell fragments in the range 2-10 um are preferred to enhance water holding capacities without compromising oil holding capacities. See the table below, which shows water and oil holding capacities of the EESF and EELF with the preferred particle size distribution:

| [g/g] | WHC | OHC |
|---|---|---|
| EESF | 0.5 | 1.5 |
| EELF | 2.5 | 1.6 |

Note
that there is an overlap in the psd of the EESF and the EELF, specifically in the range 1-4 um. This is more evident when low intensity separations are used (see FIG. 12). Therefore, it is preferred to use medium intensity separations.

Figure 15:
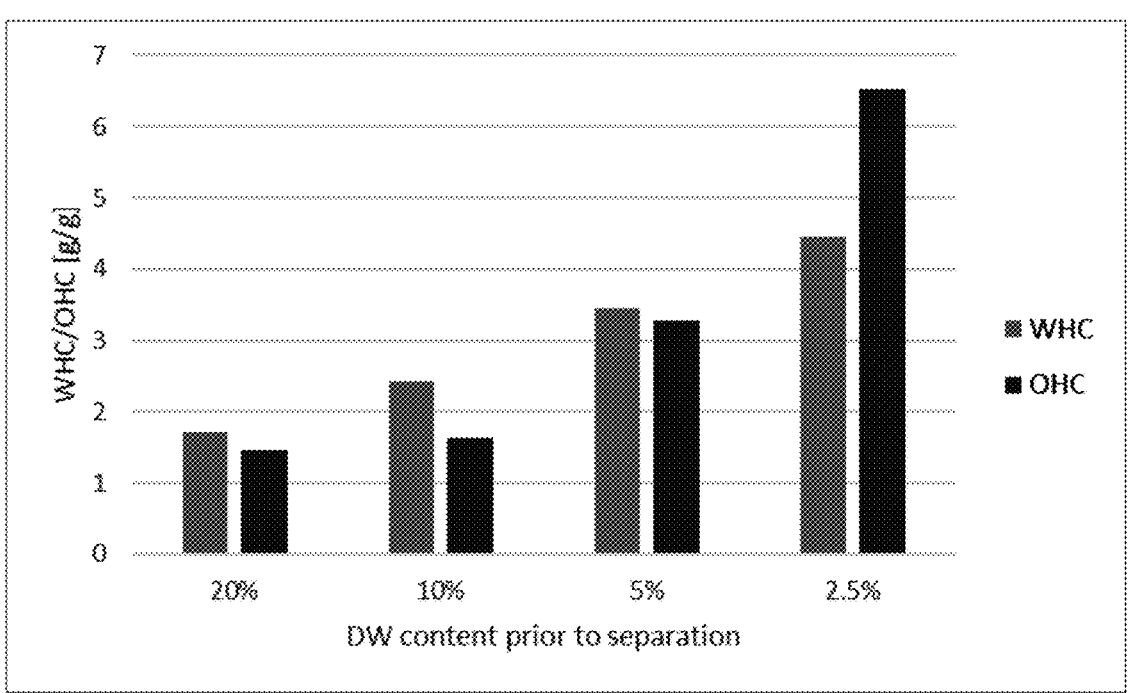
FIG. 15 shows water holding capacity and oil holding capacity of the EELF of a yeast preparation under separation at different dilution conditions.
Figure 16:
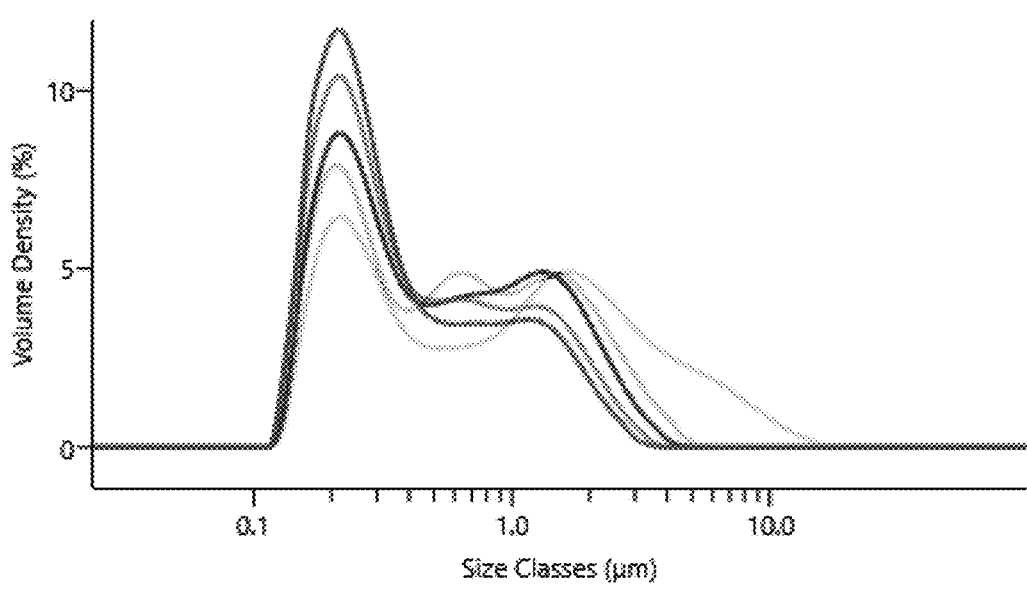
FIG. 16 shows particle size distribution of the EESF of a yeast preparation under separation at different dilution conditions.
Figure 17:
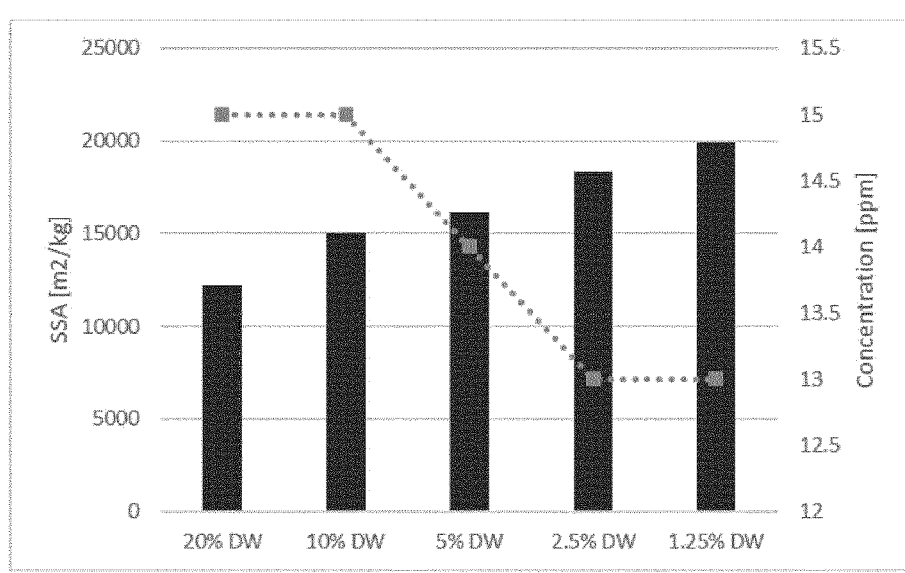
FIG. 17 shows specific surface area and concentration of different fractions of a yeast preparation under separation at different dilution conditions.
Figure 18:
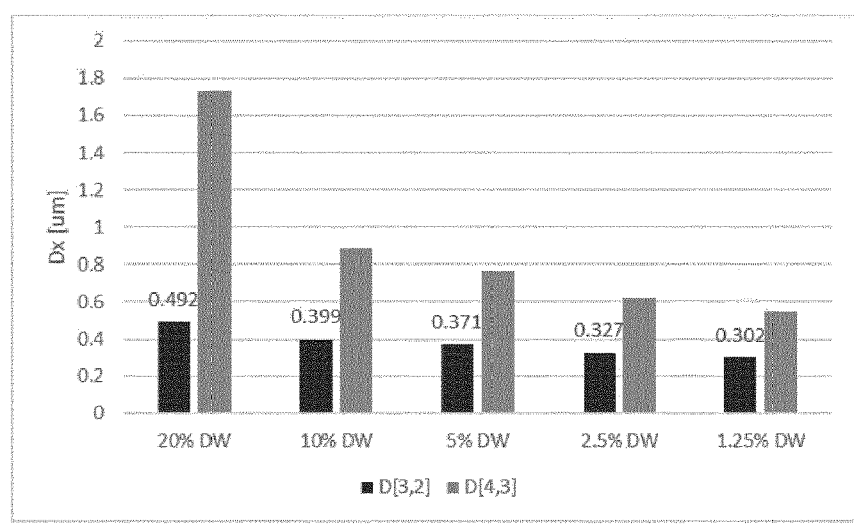
FIG. 18 shows particle size distribution of a yeast preparation under separation at different dilution conditions.

Separation can also be carried out at different dilutions to modify functional properties of the fractions. See FIGS. 14-18. For example, the separation can be performed at dry weight (DW) contents varying from 20% to 2.5%. By decreasing the DW content before separation (which is equivalent to increasing the dilution extent), the gelation properties and the water holding capacity of the EELF is enhanced. As a consequence, the functional properties in the EESF are deteriorated. See FIG. 14. Conversely, water holding capacity and oil holding capacities in the EELF are particularly improved when the separation is conducted at low DW contents. See FIG. 15.

The ranges of psd of the EESF and EELF remains practically unaffected when different dilution levels are implemented. Only the relative contribution of the main peaks in the multimodal distribution change. The contribution of the particles with a peak at ~0.2 um vs the particles with a broad peak at ~1.5-2 um increases with higher dilution levels. See FIG. 16. Similarly, higher dilution levels lead to a higher total specific surface area (SSA)—shown in FIG. 17—and the D[3,2] and D[4,3] decrease with increasing dilution levels (shown in FIG. 18).

Other Microorganisms

Although the examples thus far have used yeast as the starting microbe, the described process can also be applied to other microorganisms in order to produce cell fragments with functional activity. The table below shows the hardness of gels obtained from the EESF of two microalgae species and one cyanobacteria species, under separation conditions according to the present invention.

| | | Gel hardness [N] of the EESF | | |
|---|---|---|---|---|
| Strain | psd* D50 | Medium Intensity | High Dilution** | High Intensity |
| *Tetraselmis* sp. | 3.15 | 0.2644 | 0.1758 | 0.0989 |
| *Chlorella vulgaris* | 4.47 | 0.0719 | No Gel*** | No Gel*** |
| *Arthrospira platensis* | 2.89 | 0.1535 | 0.1024 | 0.1048 |

*psd: particle size distribution after disintegration
**High dilution: DW content before S/L separation adjusted to 2.5%
***No Gel: although gelation is observed, the resulting material could not be measured using texture profile analysis (TPA).

Furthermore, a higher dilution prior to the S/L separation, is advantageous to enhance the functional properties of the EELF, for example the gelation hardness:

| | Gel hardness [N] of the EELF | | |
|---|---|---|---|
| Strain | Medium Intensity | High Dilution | High intensity |
| *Tetraselmis* sp. | No Gel* | No Gel* | No Gel* |
| *Chlorella vulgaris* | 0.0599 | 0.2433 | 0.092 |
| *Arthrospira platensis* | No Gel* | 0.1543 | 0.0741 |

*No Gel: although gelation is observed, the resulting material could not be measured using texture profile analysis (TPA).

Figure 19:
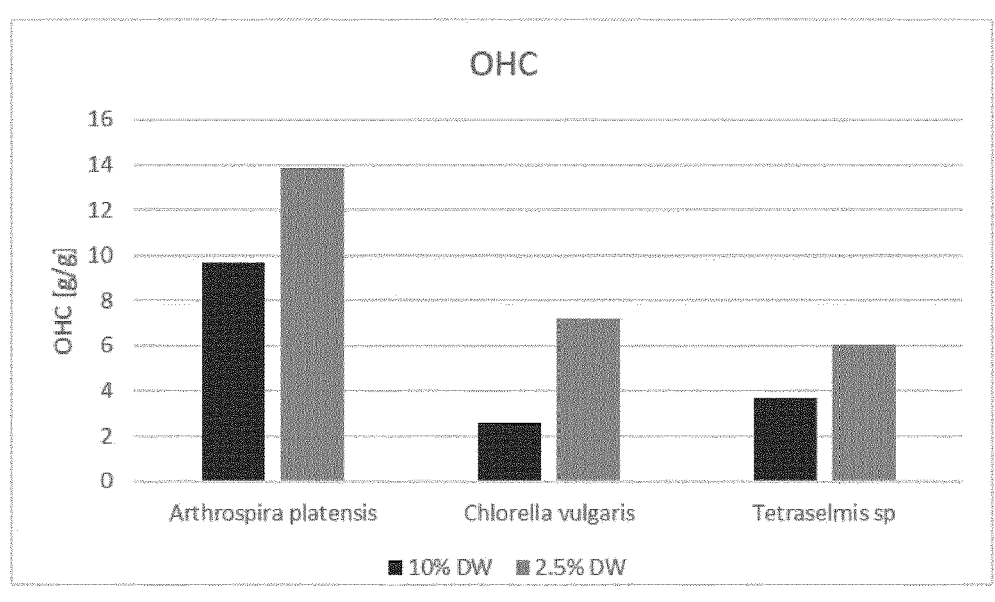
FIG. 19 shows oil holding capacity of microbial preparations from different microbes after separation at different dilution conditions.

Moreover, adjusting the dilution level prior to the S/L separation step can be used advantageously to adjust other functional properties, for example the oil holding capacity (OHC). See FIG. 19.

Extended Cell Disintegration

The cell disintegration step can be further extended in order to enhance the functional properties of the EELF. As an example, the psd can be modified over a period of 240 min in order to yield a EELF with superior gel hardness, water holding capacity WHC and oil holding capacity OHC.

| | | | | EELF | | |
|---|---|---|---|---|---|---|
| Time [min] | D [3,2] | Dx (50) | pH | gel hardness [N] | WHC [g/g] | OHC [g/g] |
| 0 | 5.1 | 5.37 | 9.12 | 0.063 | 3.47 | 1.12 |
| 60 | 1.68 | 3.21 | 6.75 | 0.185 | 4.76 | 1.86 |
| 180 | 0.559 | 1.26 | 6.53 | 0.4724 | 5.08 | 2.17 |
| 240 | 0.531 | 1.16 | 6.45 | 0.6082 | 5.99 | 3.44 |

Figure 20:
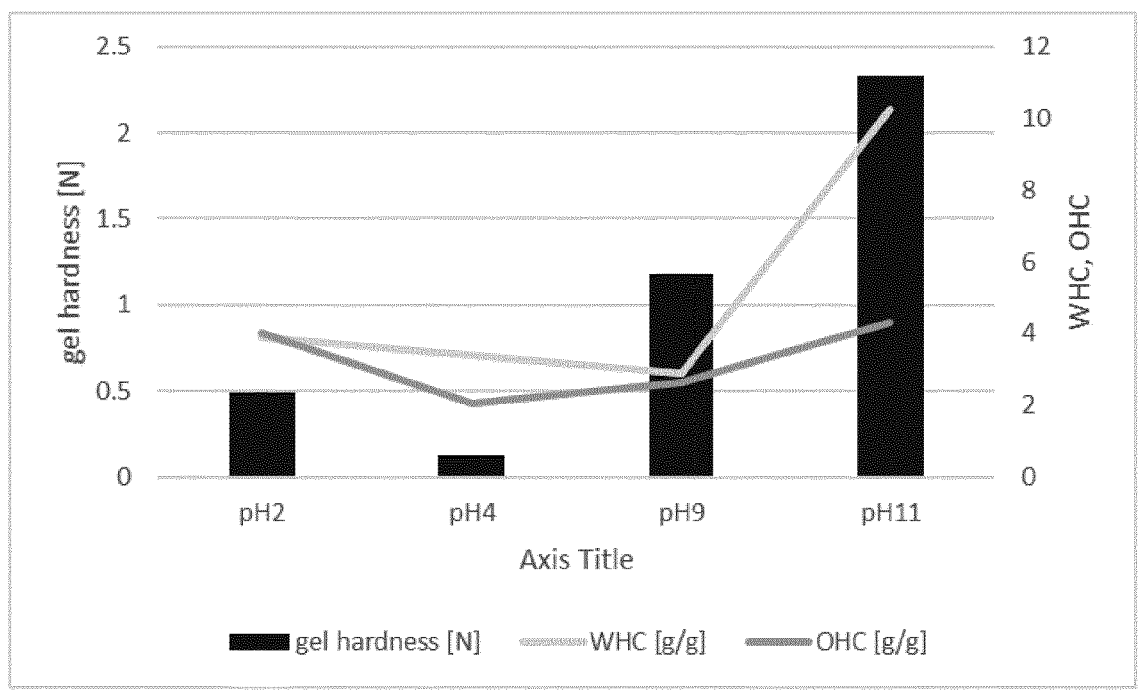
FIG. 20 shows gel hardness, and oil and water holding capacity of yeast preparations after disruption at different pH levels.
Figure 21A:
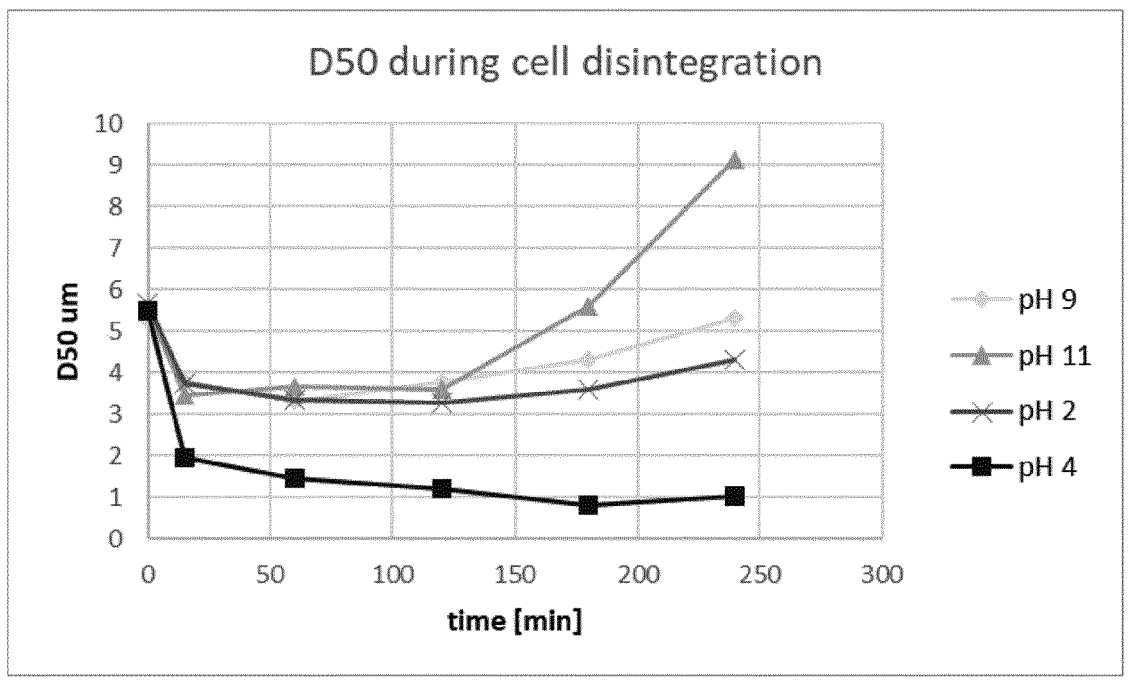
FIGS. 21A and 21B show particle size distribution—d50 and D[3,2]—over time of yeast disrupted at different pH levels.
Figure 21B:
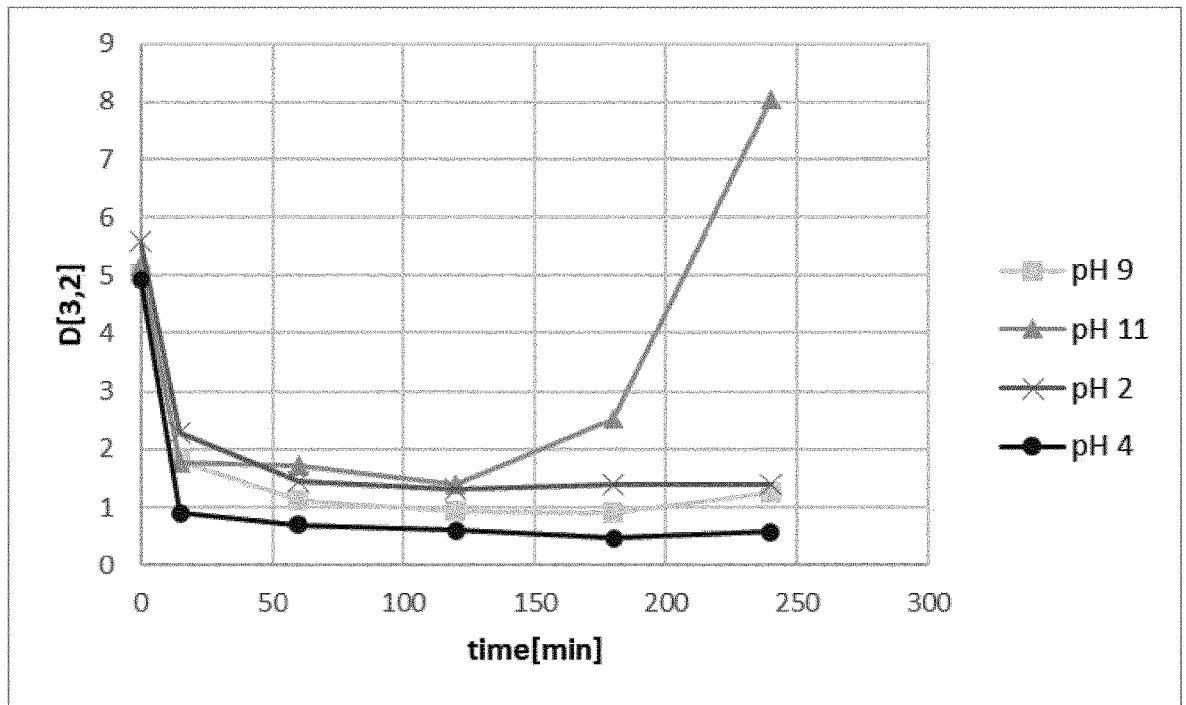

By performing the cell disintegration at alkaline conditions, preferentially at a pH>9, and by conducting the S/L separation at low DW contents (<5%), the functional properties of the EELF are significantly enhanced. See FIG. 20. At alkaline pH, however, the psd during the course of extended cell disintegration shows a unique trend. Instead of a steady decrease of the particle sizes, expected for a micronization process, the particles tend to aggregate. This effect is particularly noticeable at pH 11—see FIG. 21.

The extended cell disintegration process conducted at pH 11, followed by S/L at high dilution levels (DW<5%) produces an EELF with superior functionality in comparison to traditional B-glucan extraction processes applied for yeast biomass. As a reference, a process involving cell autolysis, cell homogenisation, alkaline extraction, acid extraction and aqueous extraction (Aut+Hom+Extr) was compared to the current proposed method (extended disintegration at pH 11 and high dilution):

| | gel hardness [N] | WHC [g/g] | OHC [g/g] |
|---|---|---|---|
| Aut + Hom + Ext | 1.69 | 8.3 | 2.55 |
| pH 11 | 2.33 | 10.24 | 4.33 |

The reference process has been reported by Saowanee Thammakiti, Manop Suphantharika, Thanaporn Phaesuwan, Cornel Verduyn. Preparation of spent brewer's yeast β-glucans for potential applications in the food industry. Food Science and Technology. Volume 39, Issue 1, January 2004, Pages 21-29.

Concentration vs Drying

The functional properties of the EESF and the EELF deteriorate as result of thermal processes such as evaporation and drying, but also freezing. It is therefore preferred to apply both fractions (EESF and EELF) as wet ingredients and to avoid processes that can induce thermal denaturation. Preferentially, both fractions should not undergo processes with temperatures above 45° C. or below 0° C.

Blending of Ingredients

Once prepared, the EELF and EESF may be mixed to obtain a microbial cell preparation according to the invention. Combining/blending of dry or wet ingredients (EESF and EELF) allows for tailored functionality to deliver, among others, texture in food applications. It is important to note that these ratios are not equal to the ratio in the disrupted slurry, in other words the streams must be separated (using centrifugation explained above) and blended back in specific ratios. Examples of this include:

Texturizer in alternative Meat Burger: Keeping the total concentration of ingredients the same but varying the ratio between EESF and EELF causes the firmness, springiness and perception of juiciness and dryness to change. This gives food formulators a range of choices to achieve the texture they are looking for. For example, mixing each in a ratio ranging from 100:0 to 0:100 shows that a mix of 70 EESF:30 EELF gives a firm, springy, not dry burger, while a mix of 40 EESF:60 EELF gives a softer, juicier, "greasy" burger. The ratios may therefore be optimised for a particular market.

Egg replacer in bakery: The expected use of the ingredients in bakery would be to use the EESF to replace egg white or whole egg in bakery applications. This is indeed proven to work well, however surprisingly using a 50:50 blend of the EESF and EELF gives better texture and performance to replace whole egg. This is counter intuitive as the main functionality needed here is heat set gelling, as the EESF has better gelation properties, the expected result is for EESF to work better than a combination.

The invention claimed is:
1. A method for preparing a microbial cell product, said method comprising:
   i) providing an aqueous suspension comprising microbial cells; and ii) subjecting said suspension to mechanical cell disintegration at a temperature in the range of 15-35° C., at a pH value in the range of 7-11, to obtain an aqueous suspension comprising disintegrated microbial cells;

iii) separating the suspension to provide an extract enriched in small cell fragments wherein the extract enriched in small cell fragments has a particle size distribution of d50 equal to or less than 500 nm, wherein said small cell fragments have a size in the range of 0.1-3 μm, and an extract enriched in large cell fragments wherein the extract enriched in large cell fragments has a particle size distribution of d50 more than 500 nm, wherein said large cell fragments have a size in the range of 3-10 μm.

2. The method according to claim 1, further including after step i) and prior to step ii), a step ia) of pretreating the aqueous suspension comprising microbial cells to obtain a pretreated aqueous suspension comprising microbial cells and a by-product.

3. The method according to claim 1, wherein the separation of step iii) is selected from the group consisting of settling, sedimentation, flocculation/coagulation, precipitation, decantation, (hydro)cyclonic separation, (air) flotation, centrifugation, filtration, and one or more combinations thereof.

4. The method according to claim 1, further including after step ii) or after step iii) a step iv), step iv) being subjecting at least one of the microbial products obtained in step ii) or step iii) to a purification treatment, independently selected from the group of treatments consisting of washing, filtering or diafiltration, adsorption, chromatography, crystallization, flocculation/coagulation, precipitation, two phase extraction, sub-critical extraction, supercritical extraction, solvent extraction distillation and one or more combinations thereof to obtain at least one purified microbial cell product.

5. The method according to claim 1, further including after step ii) or step iii), a step vi) being subjecting at least one of the microbial products obtained in step ii) or step iii), to drying.

6. The method according to claim 1, wherein the microbial cells are selected from unicellular or colonial prokaryotes and eukaryotes and one or more combinations thereof.

7. The method according to claim 6, wherein the microbial cells are yeast.

8. The method according to claim 1, wherein the mass concentration of microbial cells in said suspension of step i) is in the range of 1-25%.

9. The method according to claim 1, wherein said mechanical cell disintegration of step ii) is performed using bead milling.

10. The method according to claim 9, wherein bead milling is carried out so as to obtain a predetermined particle size distribution of the suspension.

11. The method according to claim 10, wherein the microbial cells are yeast, and the predetermined particle size distribution after step ii) is D10<0.5 um, D50<4.5 um, D90<7.5 um and D[3,2]<2, D[4,3]<4.5.

12. The method according to claim 9, wherein bead milling is carried out at pH>9 for a period of time sufficient to induce particle agglomeration and in which the dry weight content prior to separation is at least 2.5%.

13. The method according to claim 1, wherein said separation treatment of step iii) is centrifuging at a centrifugal force equal to or smaller than 4000 relative centrifugal force (rfc).

14. The method according to claim 13, wherein said centrifuging takes place for a period of time equal to or shorter than 20 min.

15. The method according to claim 1, further comprising adjusting the water content of the disintegrated cell suspension prior to the separation step iii).

16. The method according to claim 1, further including after step iii) a step v) of combining at least a portion of the extract enriched in small cell fragments and an extract enriched in large cell fragments.

17. The method according to claim 16, further comprising incubating the extract enriched in small cell fragments at below 25° C. for at least 60 minutes prior to the combining step v).

18. The method according to claim 16, further including after step ii) or after step iii) a step iv), step iv) being subjecting at least one of the microbial products obtained in step ii) or step iii) to a purification treatment, independently selected from the group of treatments consisting of washing, filtering, diafiltration, adsorption, chromatography, crystallization, flocculation/coagulation, precipitation, two phase extraction, sub-critical extraction, supercritical extraction, solvent extraction distillation and one or more combinations thereof to obtain at least one purified microbial cell product.

19. The method according to claim 18, further including after step iv) or step v), a step vi) of subjecting at least one of the microbial products obtained step iv) or step v) to drying.

20. The method according to claim 16, further including after step v), a step vi) of subjecting at least one of the microbial products obtained step v) to drying.

* * * * *